(12) United States Patent
Gillespie et al.

(10) Patent No.: US 7,790,711 B2
(45) Date of Patent: Sep. 7, 2010

(54) INHIBITORS OF 11β-HYDROXYSTEROID DEHYDROGENASE

(75) Inventors: Paul Gillespie, Westfield, NJ (US); Kevin Richard Guertin, Verona, NJ (US); Lida Qi, Leonia, NJ (US); Qiang Zhang, Parsippany, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 228 days.

(21) Appl. No.: 12/172,389

(22) Filed: Jul. 14, 2008

(65) Prior Publication Data
US 2009/0023709 A1    Jan. 22, 2009

Related U.S. Application Data

(60) Provisional application No. 60/950,168, filed on Jul. 17, 2007.

(51) Int. Cl.
*A61K 31/55* (2006.01)
*A61K 31/4439* (2006.01)
*A61K 31/4155* (2006.01)
*A61P 3/10* (2006.01)
*C07D 231/02* (2006.01)
*C07D 401/06* (2006.01)
*C07D 413/02* (2006.01)
*C07D 401/04* (2006.01)

(52) U.S. Cl. .............. 514/217.09; 514/236.5; 514/326; 514/341; 514/403; 540/602; 544/140; 546/211; 546/275.4; 548/364.1; 548/371.7

(58) Field of Classification Search ............ None
See application file for complete search history.

(56) References Cited

U.S. PATENT DOCUMENTS

| | | | |
|---|---|---|---|
| 2005/0245532 A1 | 11/2005 | Hoff | |
| 2005/0245533 A1 | 11/2005 | Hoff | |
| 2005/0245534 A1 | 11/2005 | Link | |
| 2005/0261302 A1 | 11/2005 | Hoff | |
| 2005/0277647 A1 | 12/2005 | Link | |
| 2006/0148871 A1 | 7/2006 | Rohde | |
| 2006/0149070 A1 | 7/2006 | Rohde | |

FOREIGN PATENT DOCUMENTS

| | | |
|---|---|---|
| WO | WO 2004056744 | 7/2004 |
| WO | WO 2004089415 | 10/2004 |
| WO | WO 2004089416 | 10/2004 |
| WO | WO 2004089470 | 10/2004 |
| WO | WO 2004098518 | 11/2004 |
| WO | WO 2004099156 | 11/2004 |
| WO | WO 2005016877 | 2/2005 |
| WO | WO 2005108359 | 11/2005 |
| WO | WO 2005108361 | 11/2005 |
| WO | WO 2006017542 | 2/2006 |
| WO | WO 2006024627 | 3/2006 |
| WO | WO 2006024628 | 3/2006 |
| WO | WO 2006048750 | 5/2006 |
| WO | WO 2006049952 | 5/2006 |
| WO | WO 2006050908 | 5/2006 |
| WO | WO 2006074244 | 7/2006 |
| WO | WO 2006/106052 | 10/2006 |
| WO | WO 2006104280 | 10/2006 |
| WO | WO 2006132197 | 12/2006 |
| WO | WO 2006/107470 | 9/2007 |
| WO | WO 2008099145 A1 | 8/2008 |

OTHER PUBLICATIONS

Saiah Eddine: *Current Medicinal Chem*, 15:7 (2008) 642-649 XP002508148.
B. Sorensen et al Bioorg Med. Chem. Lett 2007, 17, 527-532.
B. Sorensen et al Bioorg Med. Chem. Lett 2006, 16, 5958-5962.
J.J. Rohde et al J. Med. Chem. 2007, 50, 149-164.
V.S.C. Yeh et al Bioorg Med. Chem. Lett 2006, 16, 5414-5419.
V.S.C. Yeh et al Bioorg Med. Chem. Lett 2006, 16, 5555-5560.
M. Augustin and P. Jeschke J. Prakt Chem. 1987, 329, 607-616.
R. Chen et al Chin. Chem. Lett 1991, 2, 269-272.
R. Chen et al Jiegou Huaxue 1991, 10, 132-5.
R. Chen and J. Wang Gaodeng Xuexiao Huaxue Xuebao 1992, 13, 923-927.
R. Chen et al Gaodeng Xuexiao Huaxue Xuebao 1992, 13, 52-55.
O. El Mahdi et al Bull. Soc. Chim. France 1995, 132, 675-680.
A. Kocwa, A. Bull. Intern. Acad. Polon. Sci., Classe Sci. Math. Nat. 1936 A 390-402.

*Primary Examiner*—Kamal A Saeed
(74) *Attorney, Agent, or Firm*—George W. Johnston; Dennis P. Tramaloni; Samuel H. Megerditchian

(57) ABSTRACT

Provided herein are compounds of the formula (I):

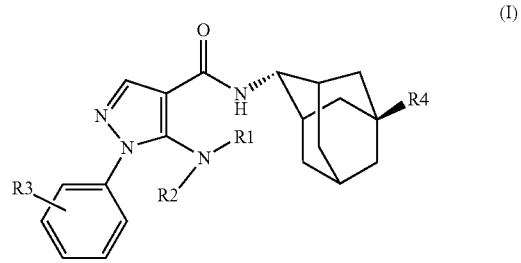

as well as pharmaceutically acceptable salts thereof, wherein the substituents are as those disclosed in the specification. These compounds, and the pharmaceutical compositions containing them, are useful for the treatment of diseases such as, for example, type II diabetes mellitus and metabolic syndrome.

15 Claims, No Drawings

INHIBITORS OF 11β-HYDROXYSTEROID DEHYDROGENASE

PRIORITY TO RELATED APPLICATION(S)

This application claims the benefit of U.S. Provisional Application No. 60/950,168, filed Jul. 17, 2007, which is hereby incorporated by reference in its entirety.

FIELD OF THE INVENTION

The invention relates to inhibitors of 11β-hydroxysteroid dehydrogenase. The inhibitors include, for example, amino-1-aryl-pyrazole-3-carboxylic acid adamantan-2-yl amides, and derivatives thereof, and are useful for the treatment of diseases such as type II diabetes mellitus and metabolic syndrome.

All documents cited or relied upon below are expressly incorporated herein by reference.

BACKGROUND OF THE INVENTION

Diabetes mellitus is a serious illness that affects an increasing number of people across the world. A recent press release by the International Diabetes Federation suggests that by 2025, there will be a total of 380 million people worldwide suffering from diabetes [http://www.idf.org/home/index.cfm?unode=E86A829B-F6FE-44FB-95EA-C3A71439F2B7]. The incidence of diabetes in many countries is escalating in parallel with an upward trend in obesity. Serious consequences of diabetes include increased risk of stroke, heart disease, kidney damage, blindness, and amputation. Cardiovascular diseases are the cause of death of more than 70% of patients with Type 2 diabetes mellitus (T2DM) [B. Pourcet et al. *Expert Opin. Emerging Drugs* 2006, 11, 379-401.]

Diabetes is characterized by decreased insulin secretion and/or an impaired ability of peripheral tissues to respond to insulin, resulting in increased plasma glucose levels. There are two forms of diabetes: insulin-dependent and non-insulin-dependent, with the great majority of diabetics suffering from the non-insulin-dependent form of the disease, known as type 2 diabetes or non-insulin-dependant diabetes mellitus (NIDDM). Because of the serious consequences, there is an urgent need to control diabetes.

The metabolic syndrome is a condition where patients exhibit more than two of the following symptoms: obesity, hypertriglyceridemia, low levels of HDL-cholesterol, high blood pressure, and elevated fasting glucose levels [R. H. Eckel *Proc. Nutr. Soc.* 2007, 66, 82-95; J.-P. Després and I. Lemieux *Nature* 2006, 444, 881-887; E. Ratto et al. *J. Am Soc. Nephrol.* 2006, 17, S120-S122; A. M. McNeill et al. *Diabetes Care* 2005, 28, 385-390]. This syndrome is often a precursor of type 2 diabetes, and has high prevalence in the United States, estimated at 24% [E. S. Ford et al. *JAMA* 2002, 287, 356]. A therapeutic agent that ameliorates the metabolic syndrome would be useful in potentially slowing or stopping the progression to type 2 diabetes.

A number of tests are used to assess diabetic patients. Fasting blood glucose levels and glucose tolerance tests are used to measure directly the amount of glucose in the blood and the ability of the body to respond to a glucose challenge. However, the level of variability of blood glucose levels is relatively high, particularly in diabetic patients, and so alternative tests are also used. One of the most common alternatives is the $HbA_{1c}$ test, which tests for the levels of glycosylated hemoglobin in the red blood cells [D. R. McCane et al. *BMJ* 1994, 308, 1323-1328; R. J. McCarter et al. *Diabetes Care* 2006, 29, 352-355]. Red blood cells have a normal life-span of 120 days in the body, and they contain hemoglobin which becomes progressively glycosylated, with the level of glycosylation correlating with the average levels of blood glucose. As a result, the $HbA_{1c}$ levels give an indication of the average levels of blood glucose over the preceding 3-4 months, and they do not fluctuate during the course of the day. The level of $HbA_{1c}$ in normal blood is approximately 5%, and the level in poorly controlled diabetic patients is 8% or above. The current guideline from the American Diabetes Association is to maintain the $HbA_{1c}$ level below 7%. This level corresponds to a mean plasma glucose level of approximately 170 mg/dL [D. E. Goldstein et al. *Diabetes Care* 2004, 27, 1761-1773].

Treatment of NIDDM generally starts with weight loss, a healthy diet and an exercise program. These factors are especially important in addressing the increased cardiovascular risks associated with diabetes, but they are generally ineffective in controlling the disease itself. There are a number of drug treatments available, including insulin, metformin, sulfonylureas, acarbose, thiazolidinediones, GLP-1 analogues, and DPP IV inhibitors. However, several of these treatments have disadvantages, and there is an ongoing need for new drugs to treat diabetes.

For example, metformin is an effective agent that reduces fasting plasma glucose levels and enhances the insulin sensitivity of peripheral tissue. Metformin has a number of effects in vivo, including an increase in the synthesis of glycogen, the polymeric form in which glucose is stored [R. A. De Fronzo *Drugs* 1999, 58 *Suppl.* 1, 29]. Metformin also has beneficial effects on lipid profile, with favorable results on cardiovascular health. Treatment with metformin leads to reductions in the levels of LDL cholesterol and triglycerides [S. E. Inzucchi *JAMA* 2002, 287, 360]. However, over a period of years, metformin loses its effectiveness [R. C. Turner et al. *JAMA* 1999, 281, 2005] and there is consequently a need for new treatments for diabetes.

Thiazolidinediones are activators of the nuclear receptor peroxisome-proliferator activated receptor-gamma (PPARγ). They are effective in reducing blood glucose levels, and their efficacy has been attributed primarily to decreasing insulin resistance in skeletal muscle [M. Tadayyon and S. A. Smith *Expert Opin. Investig. Drugs* 2003, 12, 307]. Three thiazolidinediones have been approved for use in the United States for the treatment of diabetes but one was subsequently withdrawn because of hepatotoxicity issues. The two currently approved drugs, pioglitazone and rosiglitazone, are effective in reducing blood sugar and $HbA_{1c}$ levels in diabetic patients [G. Boden and M. Zhang *Expert Opin. Investig. Drugs* 2006, 15, 243-250; B. Pourcet et al. *Expert Opin. Emerging Drugs* 2006, 11, 379-401]. However, a period of 3-4 months is required before full efficacy is seen [G. Boden and M. Zhang *Op. Cit.*], and one disadvantage associated with the use of thiazolidinediones is weight gain.

Sulfonylureas bind to the sulfonylurea receptor on pancreatic beta cells, stimulate insulin secretion, and consequently reduce blood glucose levels. Weight gain is also associated with the use of sulfonylureas [S. E. Inzucchi *JAMA* 2002, 287, 360] and, like metformin, they lose efficacy over time [R. C. Turner et al. *JAMA* 1999, 281, 2005]. A further problem often encountered in patients treated with sulfonylureas is hypoglycemia [M. Salas J. J. and Caro Adv. *Drug React. Tox. Rev.* 2002, 21, 205-217].

Acarbose is an inhibitor of the enzyme alpha-glucosidase, which breaks down disaccharides and complex carbohydrates in the intestine. It has lower efficacy than metformin or the sulfonylureas, and it causes intestinal discomfort and diarrhea which often lead to the discontinuation of its use [S. E. Inzucchi *JAMA* 2002, 287, 360]

Although drugs have been approved for the treatment of diabetes using a number of different mechanisms, and many other drugs are being evaluated clinically, there remains a need to invent new compounds for the treatment of diabetes. It has recently been disclosed that the results of the United Kingdom Prospective Study indicate that over time, a decline is seen in the beta cell function of diabetic patients irrespective of whether they were being treated with diet, sulfonylureas, metformin, or insulin [R. R. Holman *Metabolism* 2006, 55, S2-S5].

One possible target for the treatment of diabetes which has received much attention recently is 11β-hydroxysteroid dehydrogenase type I (11β-HSD1) [see for example M. Wang *Curr. Opin. Invest. Drugs* 2006, 7, 319-323]. 11β-HSD1 is an enzyme that catalyzes the reduction of cortisone to cortisol (or dehydrocorticosterone to corticosterone in rodents). Cortisol is a corticosteroid hormone produced in the adrenal gland, and it has been shown to increase levels of glucose production, mostly by increasing gluconeogenesis [S. Khani and J. A. Tayek *Clinical Sci.* 2001, 101, 739-747]. A second enzyme, 11β-hydroxysteroid dehydrogenase type II (11β-HSD2) is responsible for the oxidation of cortisol to cortisone. The enzymes have low homology and are expressed in different tissues. 11β-HSD1 is highly expressed in a number of tissues including liver, adipose tissue, and brain, while 11β-HSD2 is highly expressed in mineralocorticoid target tissues, such as kidney and colon. 11β-HSD2 prevents the binding of cortisol to the mineralocorticoid receptor, and defects in this enzyme have been found to be associated with the syndrome of apparent mineralocorticoid excess (AME).

There is evidence from transgenic mice, and also from small clinical studies in humans, that confirm the therapeutic potential of the inhibition of 11β-HSD1 for the treatment of Type 2 Diabetes mellitus.

Experiments with transgenic mice indicate that modulation of the activity of 11β-HSD1 could have beneficial therapeutic effects in diabetes and in the metabolic syndrome. For example, when the 11β-HSD1 gene is knocked out in mice, fasting does not lead to the normal increase in levels of G6Pase and PEPCK, and the animals are not susceptible to stress- or obesity-related hyperglycemia. Moreover, knockout animals which are rendered obese on a high-fat diet have significantly lower fasting glucose levels than weight-matched controls (Y. Kotolevtsev et al. *Proc. Natl. Acad. Sci. USA* 1997, 94, 14924). 11β-HSD1 knockout mice have also been found to have improved lipid profile, insulin sensitivity, and glucose tolerance (N. M. Morton et al. *J. Biol. Chem.* 2001, 276, 41293). The effect of overexpressing the 11β-HSD1 gene in mice has also been studied. These transgenic mice displayed increased 11β-HSD1 activity in adipose tissue, and they also exhibit visceral obesity which is associated with the metabolic syndrome. Levels of the corticosterone were increased in adipose tissue, but not in serum, and the mice had increased levels of obesity, especially when on a high-fat diet. Mice fed on low-fat diets were hyperglycemic and hyperinsulinemic, and also showed glucose intolerance and insulin resistance (H. Masuzaki et al. *Science,* 2001, 294, 2166).

The effects of the non-selective 11β-hydroxysteroid dehydrogenase inhibitor carbenoxolone have been studied in a number of small trials in humans. In one study, carbenoxolone was found to lead to an increase in whole body insulin sensitivity, and this increase was attributed to a decrease in hepatic glucose production (B. R. Walker et al. *J. Clin. Endocrinol. Metab.* 1995, 80, 3155). In another study, decreased glucose production and glycogenolysis in response to glucagon challenge were observed in diabetic but not healthy subjects (R. C. Andrews et al. *J. Clin. Enocrinol. Metab.* 2003, 88, 285). Finally, carbenoxolone was found to improve cognitive function in healthy elderly men and also in type 2 diabetics (T. C. Sandeep et al. *Proc. Natl. Acad. Sci USA* 2004, 101, 6734).

A number of non-specific inhibitors of 11β-HSD 1 and 11I - HSD2 have been identified, including glycyrrhetinic acid, abietic acid, and carbenoxolone. In addition, a number of selective inhibitors of 11β-HSD 1 have been found, including chenodeoxycholic acid, flavanone and 2'-hydroxyflavanone (S. Diederich et al. *Eur. J. Endocrinol.* 2000, 142, 200 and R. A. S. Schweizer et al. *Mol. Cell. Endocrinol.* 2003, 212, 41).

A need exists in the art, therefore, for 11β-HSD1 inhibitors that have efficacy for the treatment of diseases such as, for example, type II diabetes mellitus and metabolic syndrome. Further, a need exists in the art for 11β-HSD1 inhibitors having IC50 values less than about 1 μM.

SUMMARY OF THE INVENTION

In an embodiment of the present invention, provided is a compound of formula (I):

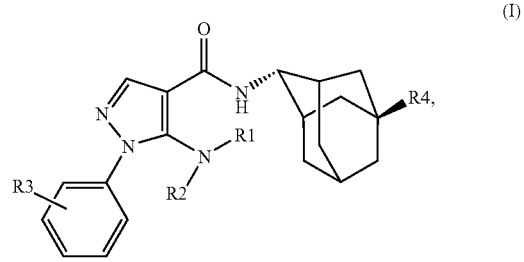

wherein:

$R_1$ is H or lower alkyl;

$R_2$ is lower alkyl, —$(CH_2)_n$-cycloalkyl, —$(CH_2)_n$-heterocycloalkyl, —$(CH_2)_n$-aryl, —$(CH_2)_n$-heteroaryl, —$(CH_2)_n$OH, —$(CH_2)_n$CH($CH_3$)OH or —$(CH_2)_n$OCH$_3$;

or $R_1$ and $R_2$, together with the N atom to which they are attached, form a 5- to 7-membered monocyclic ring, which contains the N atom to which $R_1$ and $R_2$ are attached, and optionally another hetero atom which is selected from O and S, unsubstituted or mono- or bi-substituted with hydroxy, lower alkyl or —$(CH_2)_n$OH;

$R_3$ is one or more substituents selected from H, halogen, lower alkyl and lower alkoxy;

$R_4$ is H, OH, NHC(=O)CH$_3$ or NHS(=O)(=O)CH$_3$;

n is 1, 2, 3 or 4;

and a pharmaceutically acceptable salt thereof.

In another embodiment of the present invention, provided is a pharmaceutical composition, comprising a therapeutically effective amount of a compound according to formula (I), or a pharmaceutically acceptable salt thereof, and a pharmaceutically acceptable carrier.

In a further embodiment of the present invention, provided is a method for treating diabetes, comprising the step of administering a therapeutically effective amount of a compound according to formula (I), or a pharmaceutically acceptable salt thereof, to a patient in need thereof.

DETAILED DESCRIPTION

The present invention is directed to inhibitors of 11β-HSD1. In a preferred embodiment, the invention provides for pharmaceutical compositions comprising compounds of the formula (I):

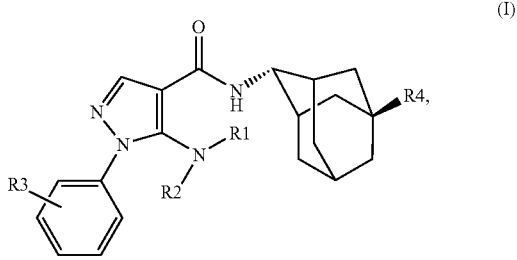

as well as pharmaceutically acceptable salts thereof, that are useful as inhibitors of 11β-HSD1.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl" means, for example, a branched or unbranched, cyclic ("cycloalkyl") or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_4$ to $C_{10}$, more preferably $C_4$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl. A preferred example of cycloalkyl includes cycloalkenyl.

In a preferred embodiment, the "cycloalkyl" moieties can optionally be substituted with one, two, three or four substituents, wherein each substituent is independently, for example, hydroxy, alkyl, alkoxy, halogen or amino, unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a cyclic alkyl ring, wherein one, two or three of the carbon ring atoms is replaced by a heteroatom such as N, O or S. Examples of heterocycloalkyl groups include, but are not limited to, morpholine, thiomorpholine, piperazine, piperidine and the like. The heterocycloalkyl groups may be unsubstituted or substituted.

As used herein, the term "lower alkyl" means, for example, a branched or unbranched, cyclic or acyclic, saturated or unsaturated (e.g. alkenyl or alkynyl) hydrocarbyl radical wherein said cyclic lower alkyl group is $C_3$, $C_4$, $C_5$, $C_6$ or $C_7$, and wherein said acyclic lower alkyl group is $C_1$, $C_2$, $C_3$ or $C_4$, and is preferably selected from methyl, ethyl, propyl (n-propyl or isopropyl) or butyl (n-butyl, isobutyl or tertiary-butyl). It will be appreciated therefore that the term "lower alkyl" as used herein includes, for example, lower alkyl (branched or unbranched), lower alkenyl (branched or unbranched), lower alkynyl (branched or unbranched), cycloloweralkyl, cycloloweralkenyl and cycloloweralkynyl.

As used herein, the term "aryl" means, for example, a substituted or unsubstituted carbocyclic aromatic group. Examples of aryl groups are phenyl, naphthyl and the like.

The term "heteroaryl", alone or in combination with other groups, means a monocyclic or bicyclic radical of 5 to 12 ring atoms having at least one aromatic ring having one, two, or three ring heteroatoms selected from N, O, and S, the remaining ring atoms being C. One or two ring carbon atoms of the heteroaryl group may be replaced with a carbonyl group. The heteroaryl group described above may be substituted independently with one, two, or three substituents, preferably one or two substituents such as, for example, halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{1-6}$ alkylthio, amino, amino $C_{1-6}$ alkyl, mono- or di-substituted amino-$C_{1-6}$ alkyl, nitro, cyano, acyl, carbamoyl, mono- or di-substituted amino, amino-carbonyl, mono- or di-substituted amino-carbonyl, aminocarbonyl $C_{1-6}$ alkoxy, mono- or di-substituted amino-carbonyl-$C_{1-6}$ alkoxy, hydroxy-$C_{1-6}$ alkyl, carboxyl, $C_{1-6}$ alkoxy carbonyl, aryl $C_{1-6}$ alkoxy, heteroaryl $C_{1-6}$ alkoxy, heterocyclyl $C_{1-6}$ alkoxy, $C_{1-6}$ alkoxycarbonyl $C_{1-6}$ alkoxy, carbamoyl $C_{1-6}$ alkoxy and carboxyl $C_{1-6}$ alkoxy, preferably halogen, hydroxy, $C_{1-6}$ alkyl, halo $C_{1-6}$ alkyl, $C_{1-6}$ alkoxy, $C_{1-6}$ alkyl sulfonyl, $C_{1-6}$ alkyl sulfinyl, $C_{16}$ alkylthio, amino, mono-$C_{1-6}$ alkyl substituted amino, di-$C_{1-6}$ alkyl substituted amino, amino $C_{1-6}$ alkyl, mono-$C_{1-6}$ alkyl substituted amino-$C_{1-6}$ alkyl, di-$C_{1-6}$ alkyl substituted amino-$C_{1-6}$ alkyl, nitro, carbamoyl, mono- or di-substituted amino-carbonyl, hydroxy-$C_{1-6}$ alkyl, carboxyl, $C_{1-6}$ alkoxy carbonyl and cyano.

The alkyl and aryl groups may be substituted or unsubstituted. Where substituted, there will generally be, for example, 1 to 3 substituents present, preferably 1 substituent. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters(e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono-or di-alkylaminocarbonyl, arylaminocarbonyl), carbamates (e.g. alkoxycarbonylamino, arloxycarbonylamino, aminocarbonyloxy, mono-or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted. Where substituted, there will generally be, for example, 1 to 3 substitutents present, preferably 1 substituent.

As used herein, the term "alkoxy" means, for example, alkyl-O— and "alkoyl" means, for example, alkyl-CO—. Alkoxy substituent groups or alkoxy-containing substituent groups may be substituted by, for example, one or more alkyl groups.

As used herein, the term "halogen" means, for example, a fluorine, chlorine, bromine or iodine radical, preferably a fluorine, chlorine or bromine radical, and more preferably a fluorine or chlorine radical.

"Pharmaceutically acceptable salt" refers to conventional acid-addition salts or base-addition salts that retain the biological effectiveness and properties of the compounds of formula I and are formed from suitable organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e. drug) into a salt is a well known technique which is used in attempting to improve properties involving physical or chemical stability, e.g., hygroscopicity, flowability or solubility of compounds. See, e.g., H. Ansel et. al., Pharmaceutical Dosage Forms and Drug Delivery Systems (6th Ed. 1995) at pp. 196 and 1456-1457.

"Pharmaceutically acceptable ester" refers to a conventionally esterified compound of formula I having a carboxyl group, which esters retain the biological effectiveness and properties of the compounds of formula I and are cleaved in vivo (in the organism) to the corresponding active carboxylic acid. Examples of ester groups which are cleaved (in this case hydrolyzed) in vivo to the corresponding carboxylic acids are those in which the hydrogen is replaced with lower alkyl which is optionally substituted, e.g., with heterocycle, cycloalkyl, etc. Examples of substituted lower alkyl esters are those in which lower alkyl is substituted with pyrrolidine, piperidine, morpholine, N-methylpiperazine, etc. The group which is cleaved in vivo may be, for example, ethyl, morpholino ethyl, and diethylamino ethyl. In connection with the present invention, —CONH$_2$ is also considered an ester, as the —NH$_2$ may be cleaved in vivo and replaced with a hydroxy group, to form the corresponding carboxylic acid.

Further information concerning examples of and the use of esters for the delivery of pharmaceutical compounds is available in Design of Prodrugs. Bundgaard H. ed. (Elsevier, 1985). See also, H. Ansel et. al., Pharmaceutical Dosage Forms and Drug Delivery Systems (6th Ed. 1995) at pp. 108-109; Krogsgaard-Larsen, et. al., Textbook of Drug Design and Development (2d Ed. 1996) at pp. 152-191.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The pharmaceutical preparations can also contain preserving agents, solubilizing agents, stabilizing agents, wetting agents, emulsifying agents, sweetening agents, coloring agents, flavoring agents, salts for varying the osmotic pressure, buffers, coating agents or antioxidants. They can also contain other therapeutically valuable substances, including additional active ingredients other than those of formula I.

The "therapeutically effective amount" or "dosage" of a compound according to this invention can vary within wide limits and may be determined in a manner known in the art.

Such dosage will be adjusted to the individual requirements in each particular case including the specific compound(s) being administered, the route of administration, the condition being treated, as well as the patient being treated. In general, in the case of oral or parenteral administration to adult humans weighing approximately 70 kg, a daily dosage of from about 0.01 mg/kg to about 50 mg/kg should be appropriate, although the upper limit may be exceeded when indicated. The dosage is preferably from about 0.3 mg/kg to about 10 mg/kg per day. A preferred dosage may be from about 0.70 mg/kg to about 3.5 mg/kg per day. The daily dosage can be administered as a single dose or in divided doses, or for parenteral administration it may be given as continuous infusion.

The compounds of the present invention can be prepared by any conventional manner. Suitable processes for synthesizing these compounds are provided in the examples. Generally, compounds of formula I can be prepared according to the Schemes described below. The sources of the starting materials for these reactions are also described.

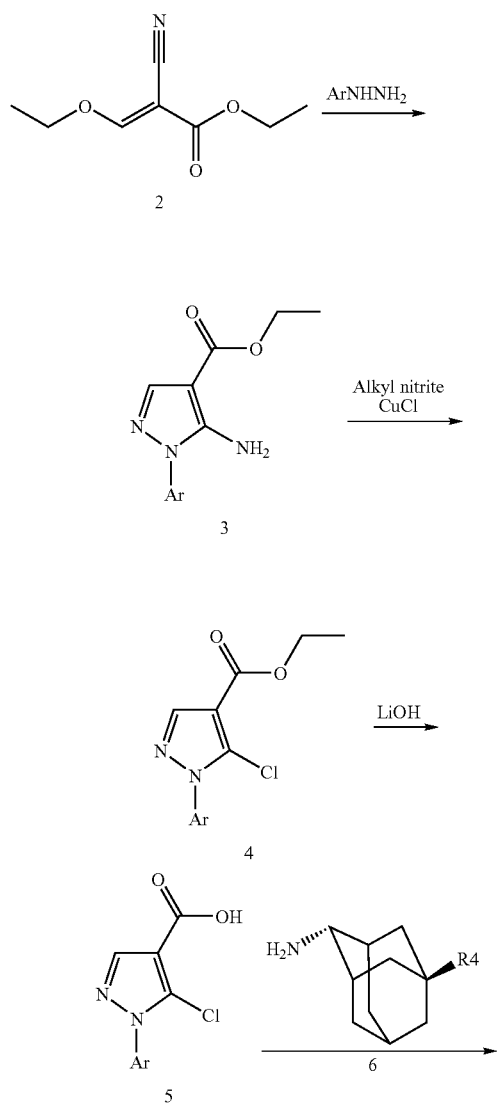

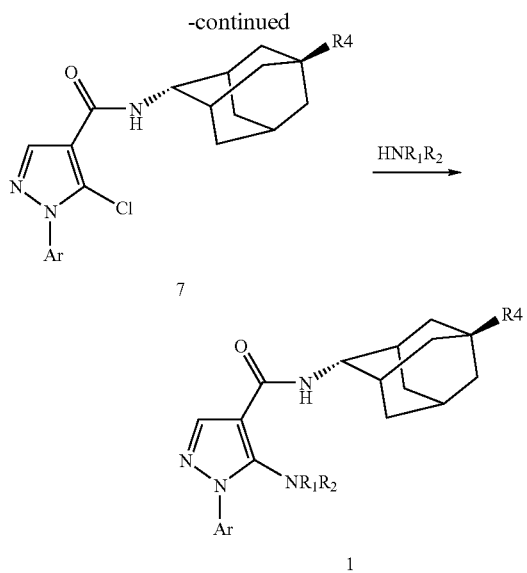

As shown in Scheme 1, a 1-aryl-5-(substituted amino)-pyrazole-4-carboxamide derivative of formula 1 can be prepared starting from ethyl (ethoxymethylene)cyanoacetate of formula 2 (which is available from Aldrich) by the following sequence of reactions:

reaction with an arylhydrazine to form the aminopyrazole of formula 3;

a Sandmeyer-type reaction of the aminopyrazole derivative to give the chloropyrazole of formula 4;

hydrolysis of the ethyl ester in the chloropyrazole of formula 4 to give the carboxylic acid of formula 5;

coupling of the carboxylic acid of formula 5 with an aminoadamantane derivative of formula 6 to give the 1-aryl-5-chloro-pyrazole-4-carboxamide of formula 7; and displacement of the chlorine in the 1-aryl-5-chloro-pyrazole-4-carboxamide of formula 7 to give the substituted 5-aminopyrazole of formula 1.

The first reaction in the sequence can be conveniently carried out by treating ethyl (ethoxymethylene)cyanoacetate of formula 2 with a hydrazine of formula $ArNHNH_2$ in an inert solvent such as ethanol at the reflux temperature. Conditions suitable for this reaction can be found in the literature, for example in A. Costanzo et al. *J. Heterocycl. Chem.* 1994, 31, 1369-1376; in M. Kopp et al. *J. Heterocycl. Chem.* 2001, 38, 1045-1050; A. Costanzo et al. *J. Heterocycl Chem.* 1992, 29, 1499-1505; in N. P. Peet et al. *J. Med. Chem.* 1992, 35, 3263-3269; and in J. R. Beck U.S. Pat. No. 4,631,343.

The Sandmeyer-type reaction of the intermediate of formula 3 involves diazotization of the amino group in the presence of a chlorinating agent such as copper(I) chloride, or copper(II) chloride, or nitrosyl chloride. The reaction is conveniently carried out by treating the compound of formula 3 with an alkyl nitrite such as tert-butyl nitrite or isoamyl nitrite in an inert solvent such as acetonitrile or a halogenated hydrocarbon (for example, carbon tetrachloride) at a temperature between about 50 degrees and about 65 degrees, in the presence of a chlorine source such as copper(I) chloride. Alternatively, the reaction can be carried out by treating the compound of formula 3 with sodium nitrite in the presence of aqueous hydrochloric acid and a chlorinating agent such as copper(II) chloride initially at a temperature preferably below 10 degrees and most preferably at about 0 degrees, and then at about 40 degrees. Conditions appropriate for this reaction can be found in the literature, for example in J.-J. Liu et al. US 2006079511; in S. Yamamoto et al. *J. Heterocycl. Chem.* 1991, 28, 1545-1547; and in I. Aoki et al. EP 220695. As a final example, the conversion of the amino-pyrazole of formula 3 to the chloro-pyrazole of formula 4 may be carried out by treating a solution of the compound of formula 3 in an inert solvent such as a chlorinated hydrocarbon (e.g., chloroform) with hydrogen chloride, and then with liquid nitrosyl chloride at a temperature below about 10 degrees and then at about room temperature. Conditions appropriate for this reaction can be found in the literature, for example in J. R. Beck et al. *J. Heterocycl Chem.* 1988, 25, 955-958 or J. R. Beck et al. *J. Heterocycl. Chem.* 1987, 24, 267-270.

The cleavage of a compound of formula 4 to the corresponding carboxylic acid of formula 5 is carried out using reaction conditions that are well known in the field of organic synthesis, many of which are outlined in "Protective Groups in Organic Synthesis" [T. W. Greene and P. G. M. Wuts, 2nd Edition, John Wiley & Sons, N.Y. 1991]. For example, the reaction can be conveniently effected by treating the compound of formula 4 with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0° C. and about room temperature, preferably at about room temperature. As another example, the ester may be treated with a strong inorganic acid, for example a hydrohalic acid such as hydrogen chloride or hydrogen bromide, in aqueous solution, preferably at the reflux temperature.

The carboxylic acid of formula 5 can be converted conveniently to the amide of formula 7 by treating the carboxylic acid of structure 5 with the hydrochloride of the adamantane derivative of formula 6 in the presence of an appropriate base, such as diisopropylethylamine, a coupling agent such as O-(benzotriazol-1-yl)- 1,1,3,3-tetramethyluronium hexafluorophosphate, and in the optional additional presence of a substance that increases the rate of the reaction, such as 1-hydroxybenzotriazole or 1-hydroxy-7-azabenzotriazole, in an inert solvent, such as a chlorinated hydrocarbon (e.g., dichloromethane) or N,N-dimethylformamide or N-methylpyrrolidinone, at a temperature between about 0 degrees and about room temperature, preferably at about room temperature. Many other choices of coupling agent are known to one of skill in the art of organic synthesis, and a discussion of many of these has been published [S.-Y. Han and Y.-A. Kim *Tetrahedron* 2004, 60, 2447-2467]. Alternatively, the reaction can be carried out by converting the carboxylic acid of formula 5 to an activated ester derivative, such as the N-hydroxysuccinimide ester, and subsequently reacting this with the adamantane derivative of formula 6 or a corresponding acid addition salt. This reaction sequence can be carried out by reacting the carboxylic acid of formula 5 with N-hydroxysuccinimide in the presence of a coupling agent such as N,N'-dicyclohexyl-carbodiimide in an inert solvent such as tetrahydrofuran at a temperature between about 0 degrees and about room temperature. The resulting N-hydroxysuccinimide ester is then treated with the adamantane derivative of formula 6 or a corresponding acid addition salt, in the presence of a base, such as an organic base (e.g., triethylamine or diisopropylethylamine or the like) in a suitable inert solvent such as N,N-dimethylformamide at around room temperature to give the 1-aryl-5-chloro-pyrazole-4-carboxamide of formula 7.

The 1-aryl-5-chloro-pyrazole-4-carboxamide of formula 7 can then be converted to the compound of the invention of formula 1 by heating it with an amine of formula $HR_1R_2$ in an inert solvent such as N-methylpyrrolidinone at a temperature about 250 degrees, under microwave irradiation.

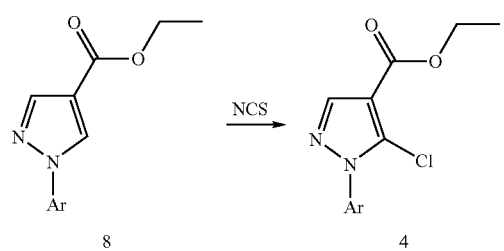

Scheme 2

An alterative preparation of the intermediate of formula 4 is shown in Scheme 2, starting from a pyrazole-4-carboxylate ester of formula 8 by treatment with a chlorinating agent. The reaction is conveniently carried out by treating the compound of formula 8 with N-chlorosuccinimide in the absence of solvent at a temperature about 120 degrees. Precise conditions for such a reaction can be found in the literature, for example in K. Morimoto et al. *J. Heterocycl. Chem.* 1997, 34, 537-540. Procedures useful for the preparation of compounds of formula 8 are outlined below.

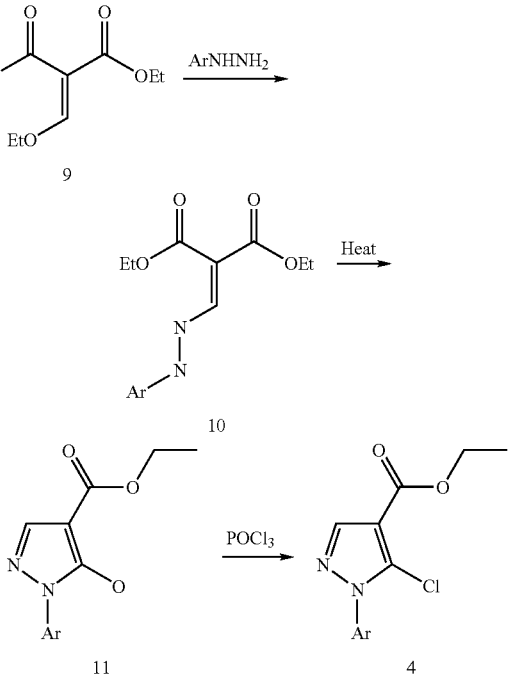

Scheme 3

A second alternative procedure for the preparation of compounds of formula 4 is shown in Scheme 3. According to this process, the reaction of commercially available diethyl ethoxymethylenemalonate of formula 9 with an arylhydrazine of formula $ArNHNH_2$ can be carried out under a variety of conditions. For example, the compound of formula 9 can be reacted with an arylhydrazine or the acid addition salt of an arylhydrazine in an inert solvent such as an alcohol (for example, ethanol). In the case where an acid addition salt of the arylhydrazine is used, then the reaction is carried out in the additional presence of a base such as a tertiary alkylamine (for example, triethylamine or diisopropylethylamine). The reaction is conveniently carried out at a temperature between about −20 degrees and about 80 degrees. Examples of conditions for this reaction can be found in the literature, for example, in R. Gehring et al. U.S. Pat. No. 4,804,398; in W. Holzer and E. Schmid *J. Heterocycl. Chem.* 1995, 32, 1341-1349. The intermediate of formula 10 is then heated to approximately 170 degrees with the evolved ethanol being removed by distillation. This process gives the 5-hydroxy-pyrazole of formula 11. Conditions for this reaction can be found in the literature, for example in R. Gehring et al. U.S. Pat. No. 4,804,398. Alternatively, the intermediate of formula 10 can be heated at reflux in ethanol in the presence of a base such as potassium carbonate to give the 5-hydroxy-pyrazole of formula 11. Conditions for this reaction can be found in the literature, for example in W. Holzer and E. Schmid *J. Heterocycl. Chem.* 1995, 32, 1341-1349. The 5-hydroxy-pyrazole of formula 11 can then be converted into the chloro-pyrazole of formula 4 through a chlorination reaction. The reaction can conveniently be carried out by heating the 5-hydroxy-pyrazole of formula 11 with a chlorinating agent such as phosphorus oxychloride in the absence of additional solvents at a temperature about 100 degrees. Precise conditions for such a reaction can be found in the literature, for example in W. Holzer and K. Hahn *J. Heterocycl. Chem.* 2003, 40, 303-308; in H. A. DeWald et al. *J. Med. Chem.* 1981, 24, 982-987.

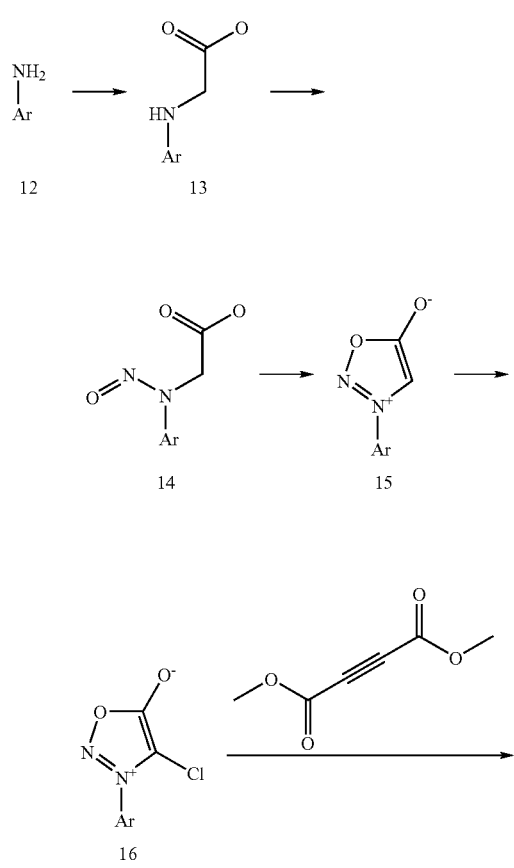

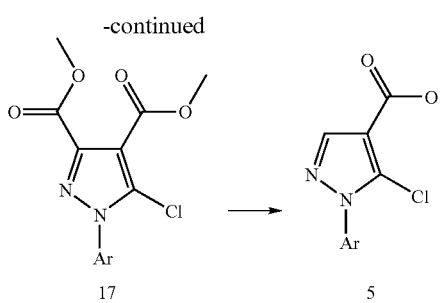

An alterative preparation of the intermediate of formula 5 is shown in Scheme 4, in which a sydnone of formula 16 undergoes a [3+2] dipolar cycloaddition reaction with dimethyl acetylenedicarboxylate followed by selective decarboxylation of the intermediate diester of formula 17. This reaction sequence starts with an aniline of formula 12 where Ar represents an aromatic group, many examples of which are commercially available. The aniline of formula 12 is converted to the N-arylglycine derivative of formula 13 by heating with chloroacetic acid in water at reflux (for details, see D. L. Hammick and D. J. Voaden *J. Chem. Soc.* 1961, 3303-3308). The N-arylglycine derivative of formula 13 is then nitrosated to give the N-nitroso derivative of formula 14 by treatment with sodium nitrite in aqueous hydrochloric acid at a temperature about 0 degrees (for details, see D. L. Hammick and D. J. Voaden *J. Chem. Soc.* 1961, 3303-3308 or F. Dumitrascu et al. *ARKIVOC* 2002, 80-86). The compound of formula 14 is then treated with acetic acid and pyridine to give the sydnone of formula 15. The sydnone is then chlorinated to give the chloro-sydnone of formula 16. The chlorination reaction can be carried out by treating the sydnone of formula 15 with chlorine in a mixture of sodium acetate and acetic acid at a temperature about room temperature (see F. Dumitrascu et al. ARKIVOC 2002, 80-86); by treating the sydnone of formula 15 with iodobenzene dichloride in a mixture of triethylamine and dichloromethane (see S. Ito and K. Turnbull *Synth. Commun.* 1996, 26, 1441-1446); or by treating the sydnone of formula 15 with N-chlorosuccinimide in an inert solvent such as dimethylformamide at a temperature about room temperature (see K. Turnbull et al. *J. Heterocycl. Chem.* 1994, 31, 1631-1636). The chloro-sydnone of formula 16 can then be treated with excess dimethyl acetylenedicarboxylate in ethylene glycol at 120 degrees to give the [3+2] dipolar cycloaddition product 17. The compound of formula 17 can then be treated with 20% aqueous hydrochloric acid at reflux to effect hydrolysis to the dicarboxylate which undergoes selective decarboxylation upon heating to about 250 degrees (bath temperature) to give the monocarboxylic acid of formula 5. Specific conditions for the reactions that lead from the chlorosydnone of formula 16 to the monocarboxylic acid of formula 5 can be found in the literature, for example in H. Dickopp *Chem. Ber.* 1974, 107, 3036-3042.

Scheme 5

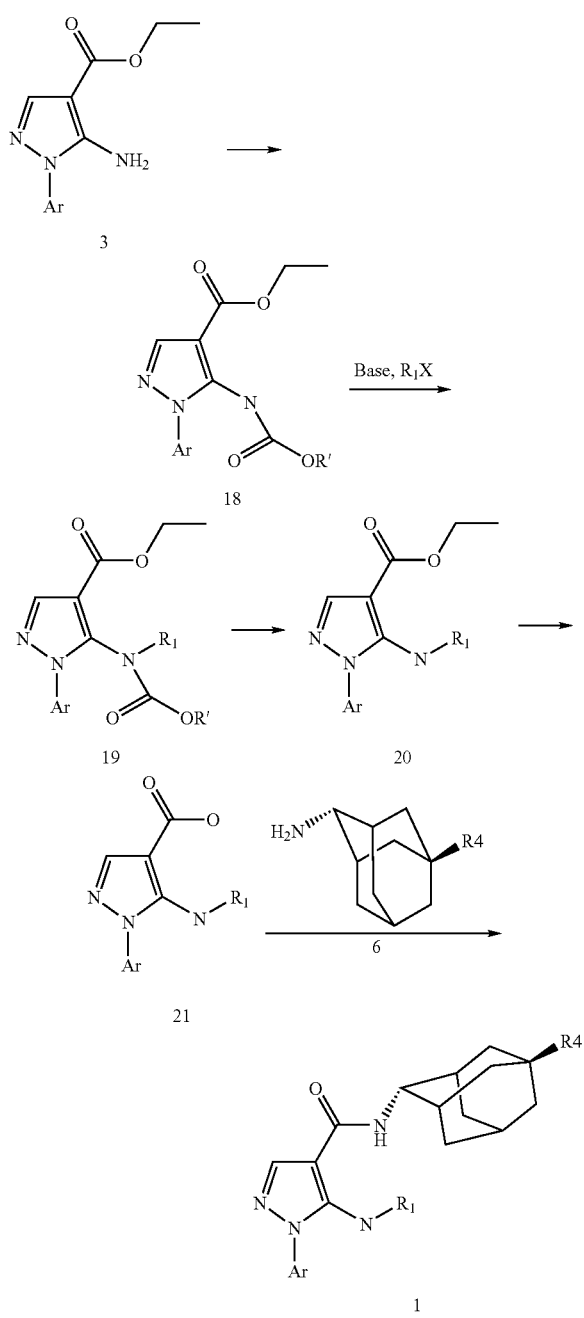

As shown in Scheme 5, a compound of the invention where $R_2$ represents hydrogen can be prepared in four steps from the 1-aryl-5-amino-pyrazole-4-carboxylate ester of formula 3 by converting the amino substituent to a carbamate which can then be alkylated to give the intermediate of formula 19. Deprotection of the carbamate and ethyl ester then gives intermediate 21 which can be coupled with an adamantan-amine of formula 6 to give the product of formula 1.

The conversion of the amine of formula 3 to the carbamate of formula 18 can be effected through any conventional means, several of which will be apparent to one of average skill in the art of organic synthesis. For example, the amine may be treated with a loweralkyl chloroformate (such as ethyl chloroformate) in the presence of a base such as sodium hydride in an inert solvent such as dimethylformamide or tetrahydrofuran. Alternatively, the amine of formula 3 can be treated with an excess of phenyl chloroformate in the presence of a base such as sodium hydride in an inert solvent such as dimethylformamide to give the bis(phenoxycarbonyl) amino derivative, as described in L. R. Hatton et al. GB 2,101,999. The reaction can also be carried out using pyridine as base and chloroform as solvent. In this case, the reaction is preferably carried out at low temperature such as at about 0 degrees. Conditions for this transformation can be found in the literature, for example in L. R. Hatton et al. U.S. Pat. No. 4,629,495. This bis(phenoxycarbonyl)amino derivative can then be treated with tert-butanol at the reflux temperature to give the intermediate of formula 18 where R' represents tert-butyl. Conditions for this transformation can be found in the literature, for example in L. R. Hatton et al. U.S. Pat. No. 4,629,495.

The alkylation of the carbamate of formula 18 with an alkylating agent of formula $R_1X$ can be effected using a variety of different procedures which are well known. The leaving group X can be a halogen (e.g., bromine or iodine) or it can be a sulfonate ester (e.g., mesylate, tosylate, or nosylate) etc. The reaction is conveniently effected by treatment of the carbamate with a base such as sodium hydride in an inert solvent such as tetrahydrofuran at a temperature between about room temperature and the reflux temperature of the solvent, depending on the reactivity of the alkylating agent.

The carbamate protective group is then removed from the carbamate of formula 19 to give the amine of formula 20 using conditions well known in the art for this transformation, which may be specific to the nature of the R' group. Many examples of appropriate conditions are outlined in the book "Protective Groups in Organic Synthesis" [T. W. Greene and P. G. M. Wuts, 2nd Edition, John Wiley & Sons, N.Y. 1991]. For example, in the case of the compound of formula 19 where R' represents tert-butyl, the protective group may be removed by treating the compound of formula 20 with an acid such as tifluoroacetic acid in an inert solvent such as a halogenated hydrocarbon (e.g., dichloromethane) at about room temperature. In the case of the compound of formula 19 where R' represents methyl or ethyl, the protective group may be removed by heating the compound of formula 19 with potassium hydroxide in ethylene glycol at about 100 degrees. Conditions for this reaction may be found in the literature, for example in K. Matsushita et al. EP 885890.

The ethyl ester in the compound of formula 20 can then be removed hydrolytically under conditions well known in the field of organic synthesis. For example, the compound of formula 20 may be treated with one equivalent of an alkali metal hydroxide, such as potassium hydroxide, sodium hydroxide, or lithium hydroxide, preferably lithium hydroxide, in a suitable solvent, such as a mixture of tetrahydrofuran, methanol, and water. The reaction can be carried out at a temperature between about 0 degrees and about room temperature, preferably at about room temperature.

As an alternative, the carbamate and ester may be removed in one process from the compound of formula 19 by subjecting the compound of formula 19 to acidic conditions, for example by heating in dilute aqueous hydrochloric acid at the reflux temperature.

The compound of the invention of formula 1 can then be prepared by reaction of the carboxylic acid of structure 21 or of an appropriate derivative thereof such as an activated ester, with an adamantane derivative of formula 6 or a corresponding acid addition salt (e.g., the hydrochloride salt) in the presence, if necessary, of a coupling agent, many examples of which are well known per se in peptide chemistry. The reaction is conveniently carried out by treating the carboxylic acid of structure 21 with the hydrochloride of the adamantane derivative of formula 6 in the presence of an appropriate base, such as diisopropylethylamine, a coupling agent such as O-(benzotriazol-1-y1)-1,1,3,3-tetramethyluronium hexafluorophosphate, and in the optional additional presence of a substance that increases the rate of the reaction, such as 1-hydroxybenzotriazole or 1-hydroxy-7-azabenzitriazole, in an inert solvent, such as a chlorinated hydrocarbon (e.g., dichloromethane) or N,N-dimethylformamide or N-methylpyrrolidinone, at a temperature between about 0 degrees and about room temperature, preferably at about room temperature. Alternatively, the reaction can be carried out by converting the carboxylic acid of formula 21 to an activated ester derivative, such as the N-hydroxysuccinimide ester, and subsequently reacting this with the adamantane derivative of formula 6 or a corresponding acid addition salt. This reaction sequence can be carried out by reacting the carboxylic acid of formula 21 with N-hydroxysuccinimide in the presence of a coupling agent such as N,N'-dicyclohexylcarbodiimide in an inert solvent such as tetrahydrofuran at a temperature between about 0 degrees and about room temperature. The resulting N-hydroxysuccinimide ester is then treated with the adamantane derivative of formula 6 or a corresponding acid addition salt, in the presence of a base, such as an organic base (e.g., triethylamine or diisopropylethylamine or the like) in a suitable inert solvent such as N,N-dimethylformamide at around room temperature.

Availability of Starting Materials

A variety of methods are known for the preparation of hydrazines and these have been reviewed in "The Chemistry of the Hydrazo, Azo, and Azoxy Groups. Part 1" [J. Timberlake and J. Stowell; S. Patai Ed.; John Wiley & Sons, Ltd. London 1975, 69-107]. Examples of processes useful for the preparation of aryl-hydrazines include diazotization of an aniline followed by reduction of the diazonium salt (P. Barraja et al. *Bioorg. Med. Chem.* 2006, 14, 8712-8728; R. V. Bonnert et al. WO 2005019171; J.-Y. Winum et al. *J. Med. Chem.* 2005, 48, 2121-2125; P. Y. S. Lam et al. *J. Med. Chem.* 2003, 46, 4405-4418); displacement of a leaving group from an alectron-deficient aryl ring (M. R. Barbachyn et al. *J. Med. Chem* 2003, 46, 284-302; M. Pal et al. *J. Med. Chem.* 2003, 46, 3975-3984; N. Pommery et al. *J. Med. Chem.* 2004, 47, 6195-6206); amination of an aniline using O-mesitylenesulfonylhydroxylamine (D. W. Brown et al. *Tetrahedron* 1993, 49, 8919-8932). By far the most commonly used method is diazotization of an aniline followed by reduction of the diazonium salt. In addition, more than a hundred substituted or unsubstituted aryl-hydrazines are listed as commercially available in the Available Chemicals Directory.

2-Adamantanamine hydrochloride is available from Aldrich.

2-Amino-5-hydroxy-adamantane (formula 22) can be prepared by hydrogenation of the imine derived from 5-hydroxy-2-adamantanone and L-S-α-methylbenzylamine according to the procedure described in L. Jaraskova et al. *Tetrahedron Lett.* 2006, 47, 8063-8067.

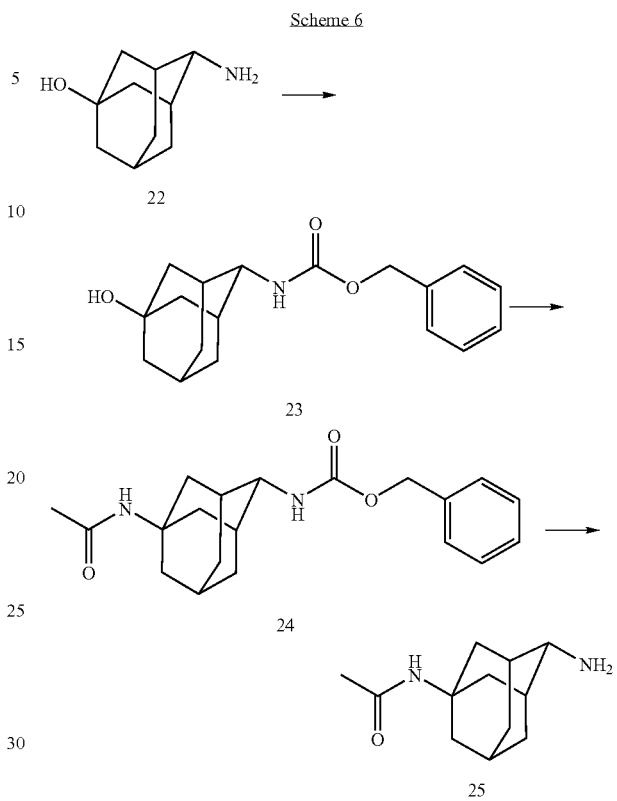

As shown in Scheme 6, 2-amino-5-acetamido-adamantane (of formula 25) can be prepared starting from 2-amino-5-hydroxy-adamantane (22). The Cbz-protected compound of formula 23 is prepared conveniently from 2-amino-5-hydroxy-adamantane by treatment with benzyl chloroformate in the presence of a base such as triethylamine in an inert solvent such as dichloromethane at about room temperature. The alcohol of formula 23 is then treated with an inorganic acid such as sulfuric acid in acetonitrile at room temperature in a reaction known as the Ritter reaction. Conditions for this reaction may be found in L. Jaroskova et al. WO 2006024627; in B. Gopalan et al. WO2006090244; and in R. K. Hill *J. Am Chem. Soc.* 1965, 87, 5646-5651. The carbobenzyloxy protective group is then removed from the compound of formula 24 using hydrogenation under noble metal catalysis to give the amine of formula 25. For example, the compound of formula 24 may be hydrogenated at approximately 50 psi in the presence of a catalytic amount of 5% palladium-on-carbon in an alcoholic solvent (such as ethanol) at room temperature.

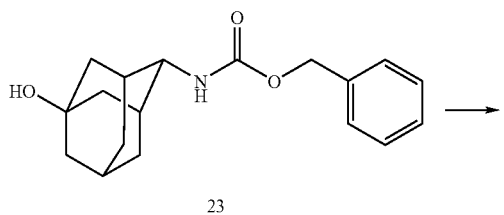

-continued

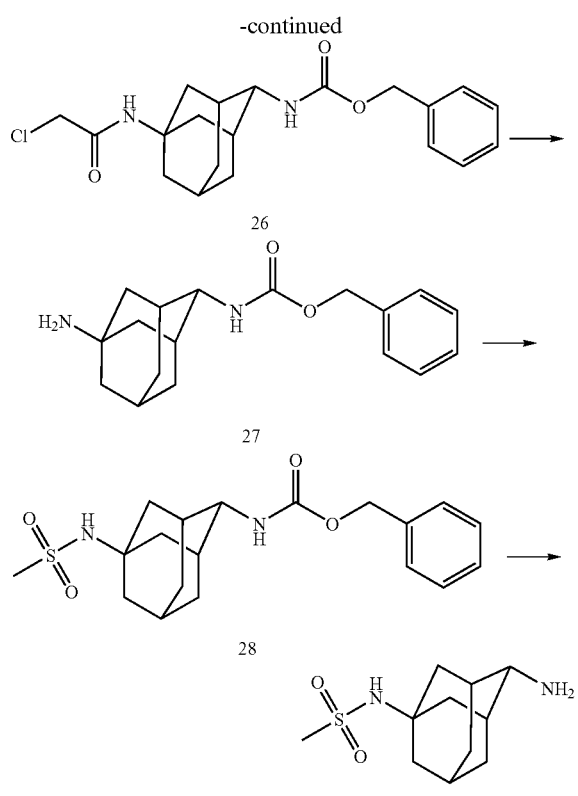

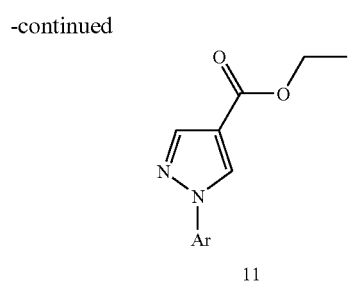

As shown in Scheme 8, a 1-aryl-pyrazole-4-carboxylate ester of formula 11 can be conveniently prepared by the reaction of (ethoxycarbonyl)-malondialdehyde with an arylhydrazine. The synthesis of (ethoxycarbonyl)-malondialdehyde is described in two steps from ethyl propiolate in S. H. Bertz et al. *J. Org. Chem.* 1982, 47, 2216-2217. The compound of formula 11 is conveniently prepared by treating (ethoxycarbonyl)-malondialdehyde with an arylhydrazine in an inert solvent such as a lower alcohol (e.g., ethanol) at room temperature. Conditions suitable for this reaction can be found in the literature, for example in W. Holzer and G. Seringer *J. Heterocycl. Chem.* 1993, 30, 865-872.

As shown in Scheme 7, the alcohol of formula 23 can be subjected to Ritter reaction conditions with chloroacetonitrile, in the presence of sulfuric acid at about room temperature, to give the chloroacetyl derivative of formula 26. This compound then undergoes reaction with thiourea in the presence of acetic acid in ethanol at a temperature between about 50 degrees and about 120 degrees to give the amine of formula 27. Conditions for the Ritter reaction and the deprotection of the chloroacetamide can be found in the literature, for example in I. R. Gladwell WO 2007010356; in B. Gopalan et al. WO2006090244; and in A. Jirgensons et al. *Synthesis* 2000, 1709-1712. The amine of formula 27 can then be treated with methanesulfonyl chloride in the presence of a base such as triethylamine or diisopropylethylamine in an inert solvent such as dichloromethane at about room temperature to give the sulfonamide of formula 28. The carbobenzyloxy protective group is then removed from the compound of formula 28 using hydrogenation under noble metal catalysis to give the amine of formula 29. For example, the compound of formula 28 may be hydrogenated at approximately 50 psi in the presence of a catalytic amount of 5% palladium-on-carbon in an alcholic solvent (such as ethanol) at room temperature.

Scheme 8

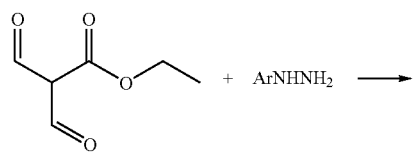

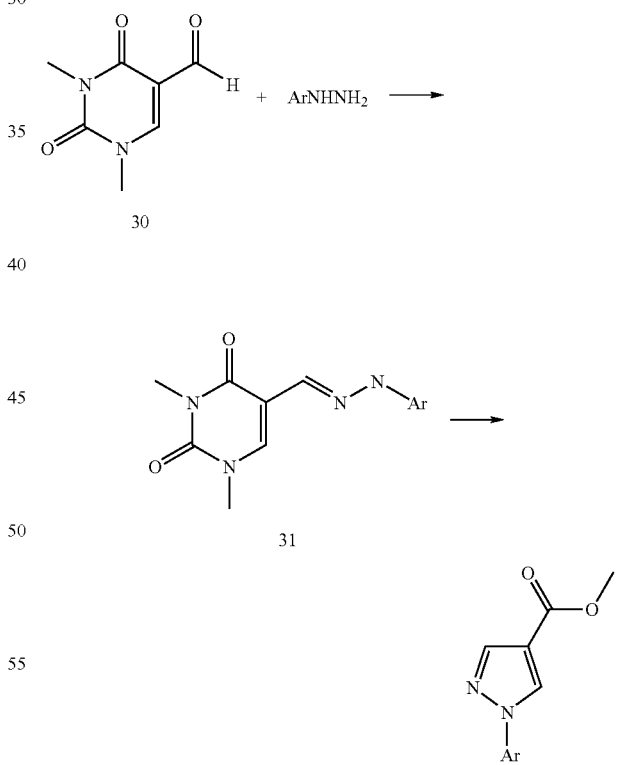

As shown in Scheme 9, a 1-aryl-pyrazole-4-carboxylate ester of formula 11 can be conveniently prepared in two steps from the commercially available 1,3-dimethyluracil-5-carboxaldehyde (of formula 30). Thus, the aldehyde is treated with an arylhydrazine of formula ArNHNH$_2$ in water in the presence of acetic acid at about 100 degrees to give the hydrazone of formula 31. This is then heated in the presence of sodium methoxide in methanol at the reflux temperature to give the 1-aryl-pyrazole-4-carboxylate ester of formula 11. Conditions suitable for this reaction can be found in the literature, for example in K. Hirota et al. *J. Chem. Soc. Perkin Trans. I* 1983, 1293-1297.

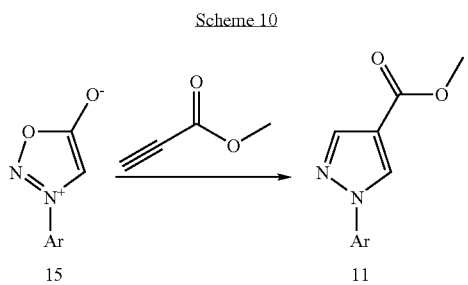

Scheme 10

As shown in Scheme 10, a 1-aryl-pyrazole-4-carboxylate ester of formula 11 can be isolated as the minor product of a [3+2] dipolar cycloaddition reaction of a sydnone of formula 15 (prepared as described above) with a loweralkyl propiolate (e.g., methyl propiolate). The reaction is conveniently carried out by treating the sydnone of formula 15 with methyl propiolate in an inert solvent such as 1,2-dichlorobenzene, isobutyl alcohol, p-xylene, or dimethylformamide at the reflux temperature. Conditions suitable for this reaction can be found in the literature, for example in E.-M. Chang et al. *Heterocycles* 2006, 68, 1007-1015.

The invention will now be further described in the Examples which follow, which are intended as an illustration only and do not limit the scope of the invention.

EXAMPLES

Reagents were purchased from Aldrich, Sigma, Bachem Biosciences, Advanced ChemTech, Lancaster and Argonaut Argogel and used without further purification. Unless otherwise indicated, all reagents were obtained from commercial sources. LC/MS (liquid chromatography/mass spectroscopy) spectra were recorded using the following system. For measurement of mass spectra the system was configured with a Micromass Platform II: API Ionization in positive electrospray (mass range: 150-1200 amu). The simultaneous chromatographic separation was achieved with the following HPLC system: Column, ES Industries Chromegabond WR C-18 3 u 120 Å (3.2×30 mm) Cartridge; Mobile Phase A: Water (0.02% TFA) and Phase B: Acetonitrile (0.02% TFA); gradient 10% B to 90% B in 3 minutes; equilibration time, 1 minute; flow rate of 2 mL/minute.

Compounds were purified using various methods of chromatography including flash column chromatography using silica gel and eluting with ethyl acetate and hexane solvent mixtures or other appropriate solvents. Certain compounds were also purified by reversed phased HPLC, using methods well known to those skilled in the art.

Intermediate 1:
5-Chloro-1-phenyl-1H-pyrazole-4-carboxylic acid ethyl ester

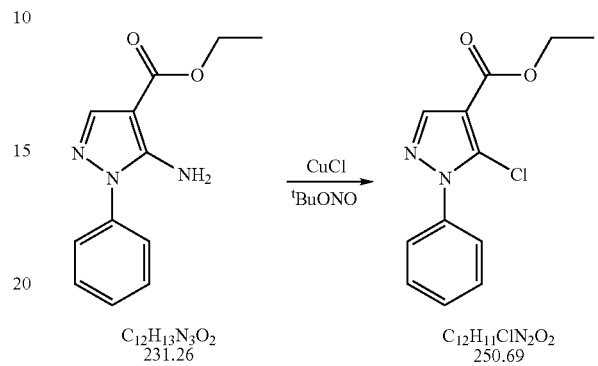

To a suspension of copper (I) chloride (5.1 g, 51.5 mmol, 1.2 equivalents) in acetonitrile (100 mL) at 0° C. was added dropwise tert-butyl nitrite (7.6 mL, 63.9 mmol, 1.5 equivalents). The reaction mixture was stirred at 0° C. for 10 minutes. A solution of 5-amino-1-phenyl-1H-pyrazole-4-carboxylic acid ethyl ester (available from Aldrich; 10.0 g, 43.2 mmol, 1 equivalent) in acetonitrile (30 mL) was added dropwise at 0° C. over 15 minutes. The reaction mixture was stirred at room temperature for 1 hour then at 65° C. for 1 hour. Following complete consumption of starting material (monitored by TLC), the reaction mixture was poured into 6N hydrochloric acid (200 mL) and extracted with dichloromethane (3×300 mL). The combined organic layers were dried over magnesium sulfate and purified by column chromatography (eluting with heptane then 20% ethyl acetate in heptane) to give 5-chloro-1-phenyl-1H-pyrazole-4-carboxylic acid ethyl ester (7.3 g, 66%), which NMR and HPLC analysis indicated was 78% pure. This material was used directly in the next step without further purification.

Intermediate 2:
5-Chloro-1-phenyl-1H-pyrazole-4-carboxylic acid

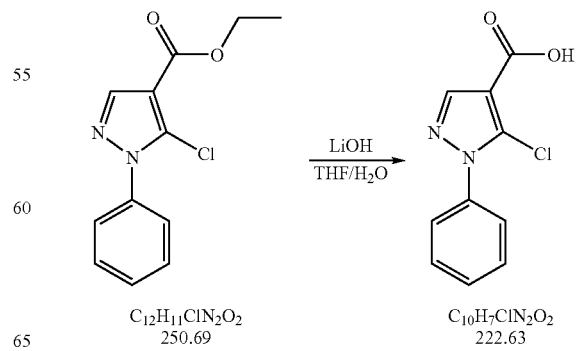

To a solution of 5-chloro-1-phenyl-1H-pyrazole-4-carboxylic acid ethyl ester (Intermediate 1; 7.3 g, 29.1 mmol) in tetrahydrofuran (70 mL) was added a solution of lithium hydroxide in water (7.3 g, 305 mmol) in water (70 mL). Methanol (~10 mL) was added dropwise to the reaction mixture until only one layer was visible. The reaction mixture was stirred at 70° C. for 1 hour (reaction progress monitored by TLC). The reaction mixture was acidified to pH 3 with 1N hydrochloric acid and washed with dichloromethane (3×200 mL). The organic layer was dried over magnesium sulfate and evaporated to give 5-chloro-1-phenyl-1H-pyrazole-4-carboxylic acid (5.8 g, 91%), which HPLC analysis indicated was 85% pure. This material was used directly in the next step without further purification.

Intermediate 3:
5-Chloro-1-phenyl-1H-pyrazole-4-carboxylic acid adamantan-2-ylamide

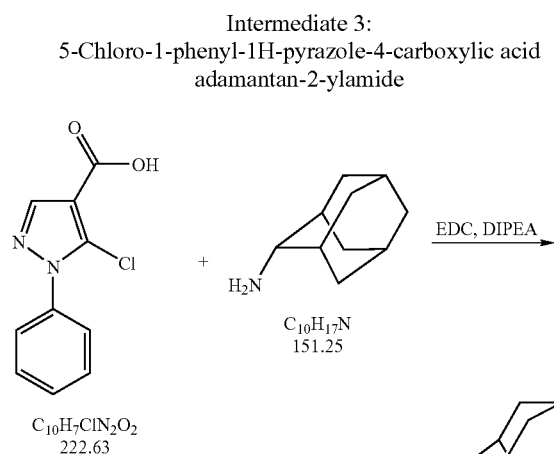

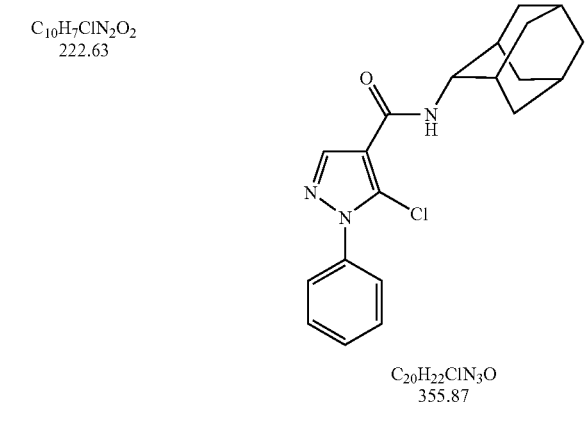

To a solution of 5-chloro-1-phenyl-1H-pyrazole-4-carboxylic acid (Intermediate 2; 5.8 g, 26.1 mmol) in tetrahydrofuran (70 mL) was added 2-adamantamine hydrochloride (available from Aldrich; 6.0 g, 32.0 mmol, 1.2 equivalents) and diisopropylethylamine (5.7 mL, 32.7 mmol, 1.2 equivalents). 1-(3-Dimethylaminopropyl)-3-ethylcarbodiimide hydrochloride (EDC; 7.5 g, 39.1 mmol, 1.5 equivalents) was added portionwise with stirring. Following complete addition of the EDC, the reaction mixture was stirred at 70° C. for ~2 hours (reaction progress monitored by TLC and LCMS). The reaction mixture was dissolved in dichloromethane (300 mL), washed with 1N hydrochloric acid (2×200 mL), and brine (200 mL), then dried over magnesium sulfate, filtered, evaporated, and purified by column chromatography (eluting with 20% ethyl acetate in heptane) to give 5-chloro-1-phenyl-1H-pyrazole-4-carboxylic acid adamantan-2-ylamide (4.2 g, 11.8 mmol, 45%), which HPLC analysis indicated was 90% pure. This material was used directly in the next step without further purification.

Procedure A

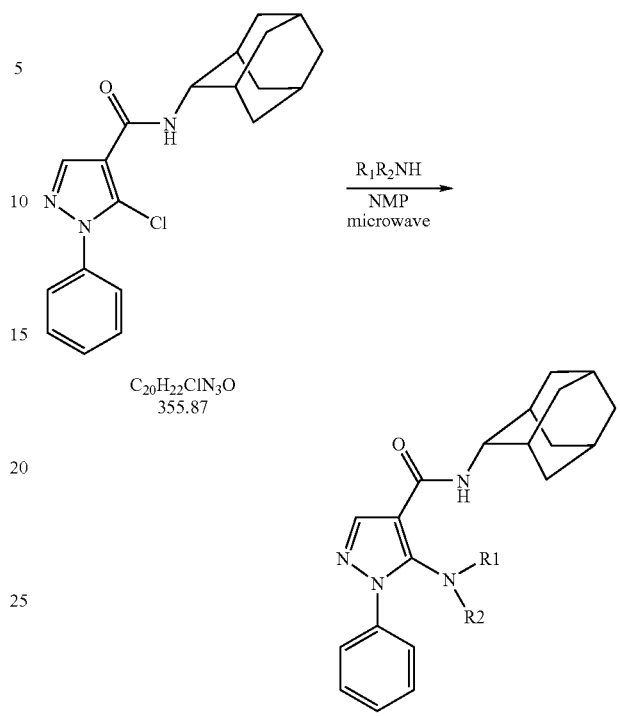

To a solution of 5-chloro-1-phenyl-1H-pyrazole-4-carboxylic acid adamantan-2-ylamide (Intermediate 3; 1 equivalent) in N-methylpyrrolidinone (10 volumes) was added the amine (R1R2NH; 20 equivalents). The reaction mixture was heated under microwave conditions (250° C., 150 W) for 20 minutes. Multiple pulses were required (generally 2-3 gave complete consumption of starting material; reactions monitored by LCMS). The compounds were purified by chromatography, eluting with the following solvent sequence: heptane; 10% ethyl acetate in heptane; 20% ethyl acetate in heptane; and 50% ethyl acetate in heptane.

Example 1

5-Isopropylamino-1-phenyl-1H-pyrazole-4-carboxylic acid adamantan-2-ylamide

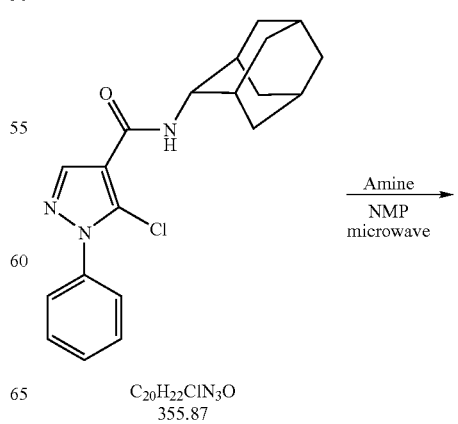

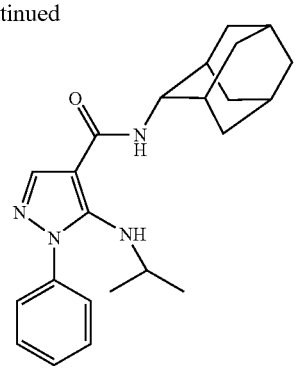

C₂₃H₃₀N₄O
378.52

5-Isopropylamino-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and isopropylamine. Mass spectrum (ES) MH+=379.

Example 2

5-Benzylamino-1-phenyl-1H-pyrazole-4-carboxylic acid adamantan-2-ylamide

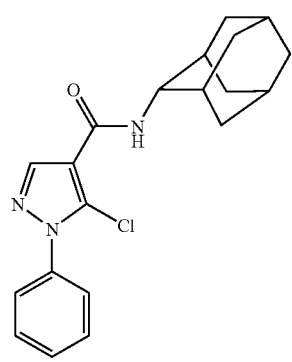

C₂₀H₂₂ClN₃O
355.87

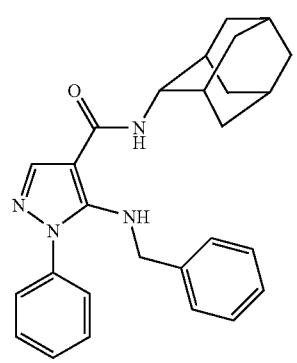

C₂₇H₃₀N₄O
426.56

5-Benzylamino-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and benzylamine. Mass spectrum (ES) MH+=427.

Example 3

1-Phenyl-5-[(pyridin-3-ylmethyl)-amino]-1H-pyrazole-4-carboxylic acid adamantan-2-ylamide

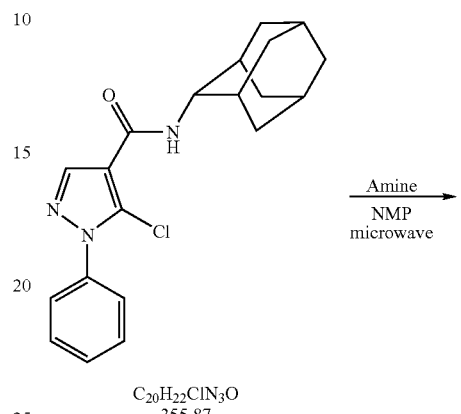

C₂₀H₂₂ClN₃O
355.87

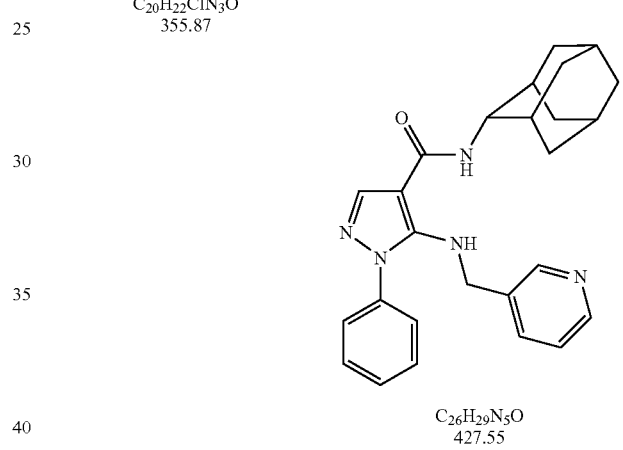

C₂₆H₂₉N₅O
427.55

Phenyl-5-[(pyridin-3-ylmethyl)-amino]-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and 3-(aminomethyl)pyridine. Mass spectrum (ES) MH+=428.

Example 4

5-(Cyclopropylmethyl-amino)-1-phenyl-1H-pyrazole-4-carboxylic acid adamantan-2-ylamide

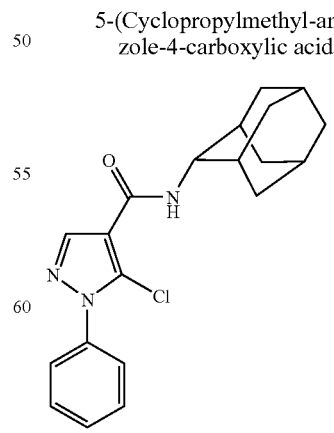

C₂₀H₂₂ClN₃O
355.87

-continued

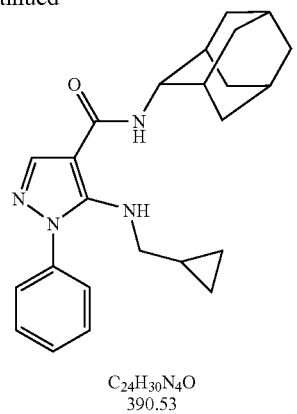

C$_{24}$H$_{30}$N$_4$O
390.53

5-(Cyclopropylmethyl-amino)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and cyclopropanemethylamine. Mass spectrum (ES) MH+=391.

Example 5

5-Cyclohexylamino-1-phenyl-1H-pyrazole-4-carboxylic acid adamantan-2-ylamide

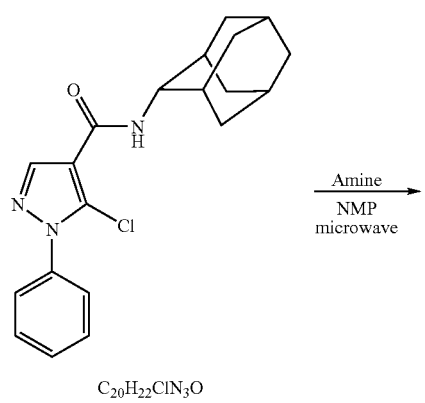

C$_{20}$H$_{22}$ClN$_3$O
355.87

C$_{26}$H$_{34}$N$_4$O
418.58

5-Cyclohexylamino-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and cyclohexylamine. Mass spectrum (ES) MH+=419.

Example 6

5-Cyclobutylamino-1-phenyl-1H-pyrazole-4-carboxylic acid adamantan-2-ylamide

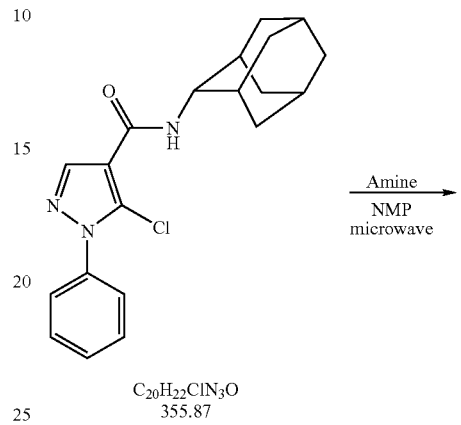

C$_{20}$H$_{22}$ClN$_3$O
355.87

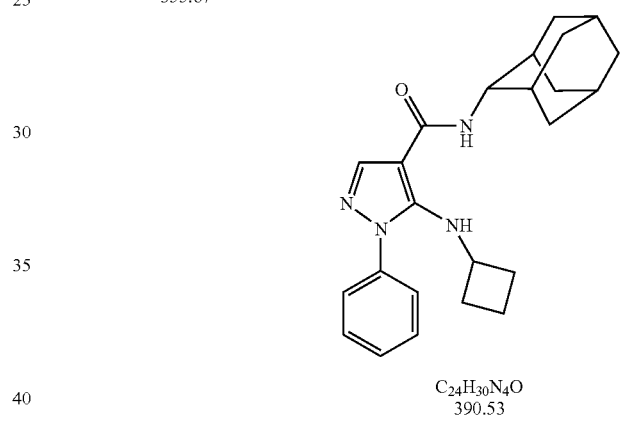

C$_{24}$H$_{30}$N$_4$O
390.53

5-Cyclobutylamino-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and cyclobutylamine. Mass spectrum (ES) MH+=391.

Example 7

5-(2,5-Dimethyl-pyrrolidin-1-yl)-1-phenyl-1H-pyrazole-4-carboxylic acid adamantan-2-ylamide

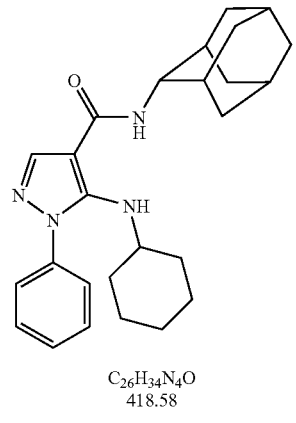

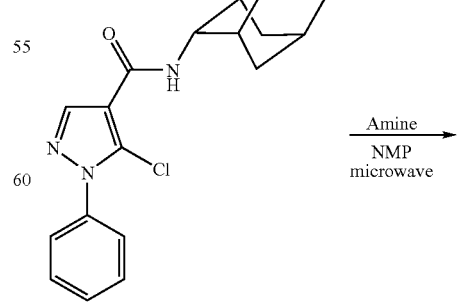

C$_{20}$H$_{22}$ClN$_3$O
355.87

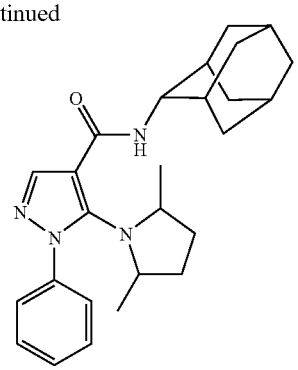

C26H34N4O
418.58

5-(2,5-Dimethyl-pyrrolidin-1-yl)-1-phenyl-1H-pyrazole-4-carboxylic acid adamant-2-ylamide was prepared using Procedure A from 5-chloro-1-phenyl-1H-pyrazole-4-carboxylic acid adamantan-2-ylamide (Intermediate 3) and 2,5-dimethylpyrrolidine. Mass spectrum (ES) MH+=419.

Example 8

5-(2-Methyl-pyrrolidin-1-yl)-1-phenyl-1H-pyrazole-4-carboxylic acid adamantan-2-ylamide

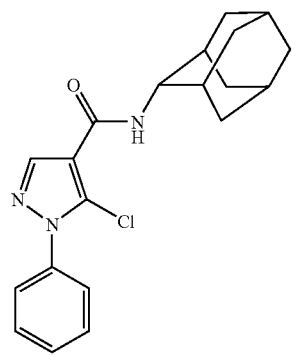

C20H22ClN3O
355.87

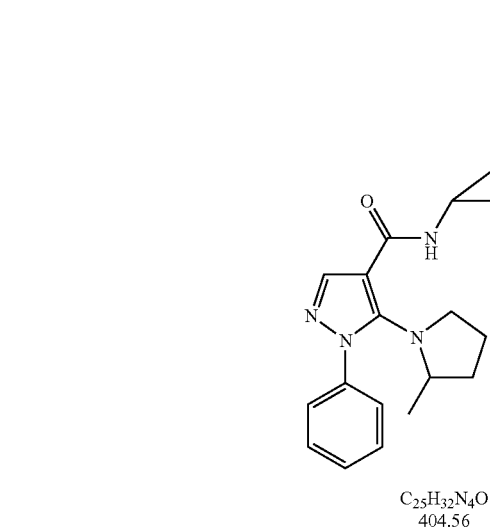

C25H32N4O
404.56

5-(2-Methyl-pyrrolidin-1-yl)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and 2-methylpyrrolidine. Mass spectrum (ES) MH+=405.

Example 9

5-(3-Methyl-piperidin-1-yl)-1-phenyl-1H-pyrazole-4-carboxylic acid adamantan-2-ylamide

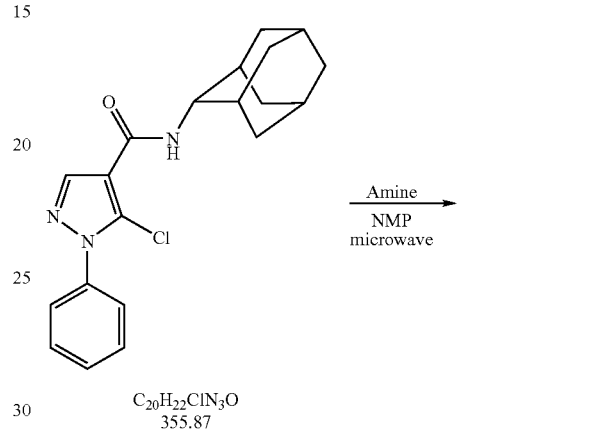

C20H22ClN3O
355.87

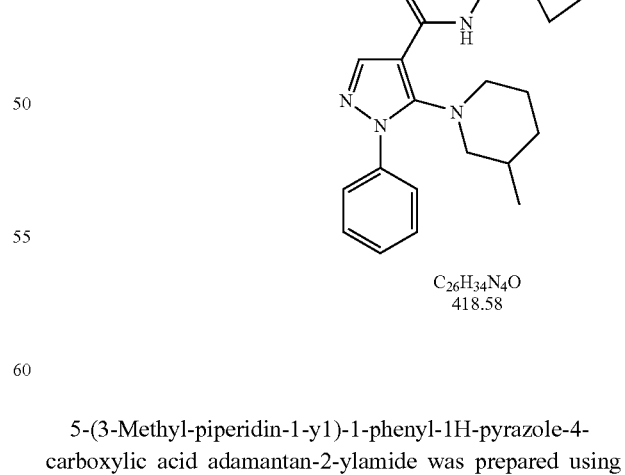

C26H34N4O
418.58

5-(3-Methyl-piperidin-1-yl)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and 3-methylpiperidine. Mass spectrum (ES) MH+=419.

Example 10

5-(Benzyl-methyl-amino)-1-phenyl-1H-pyrazole-4-carboxylic acid adamantan-2-ylamide

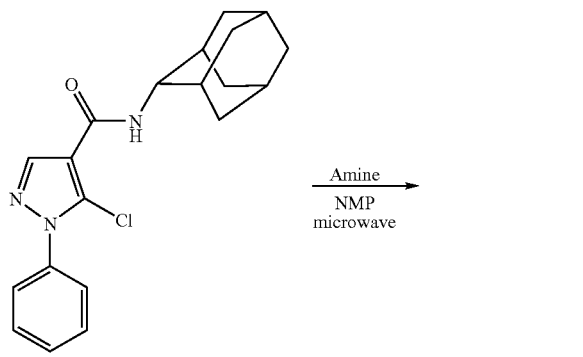

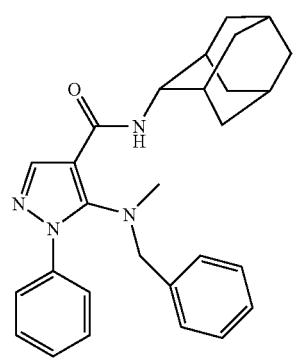

5-(Benzyl-methyl-amino)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and N-methylbenzylamine. Mass spectrum (ES) MH+=441.

Example 11

5-(Methyl-phenethyl-amino)-1-phenyl-1H-pyrazole-4-carboxylic acid adamantan-2-ylamide

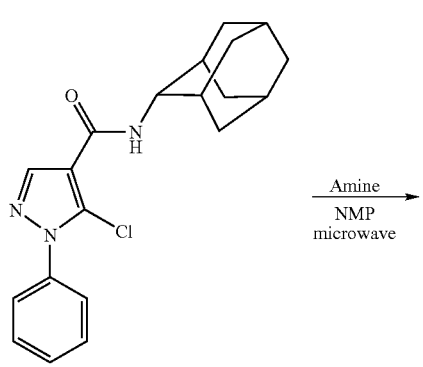

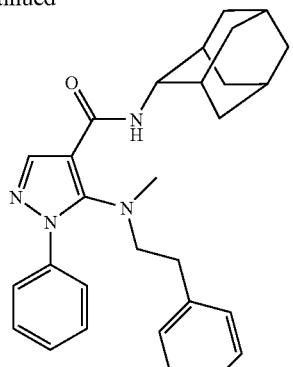

5-(Methyl-phenethyl-amino)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and N-methylphenethylamine. Mass spectrum (ES) MH+=455.

Example 12

5-(2,6-Dimethyl-morpholin-4-yl)-1-phenyl-1H-pyrazole-4-carboxylic acid adamantan-2-ylamide

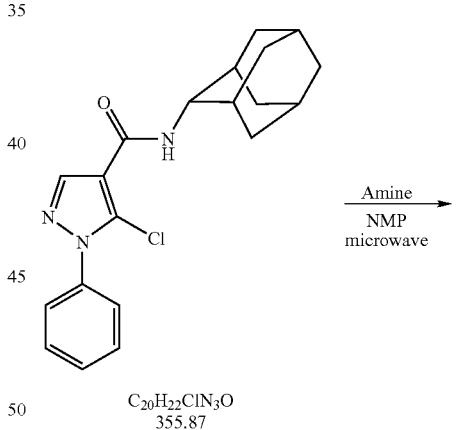

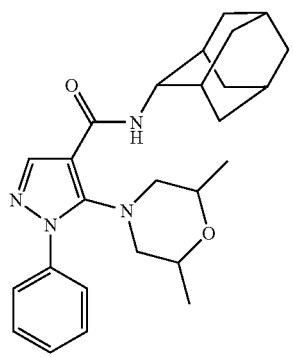

5-(2,6-Dimethyl-morpholin-4-yl)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and 2,6-dimethylmorpholine. Mass spectrum (ES) MH+=435.

Example 13

1-Phenyl-5-pyrrolidin-1-yl-1H-pyrazole-4-carboxylic acid adamantan-2-ylamide

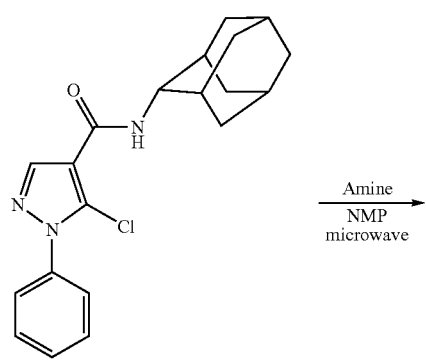

$C_{20}H_{22}ClN_3O$
355.87

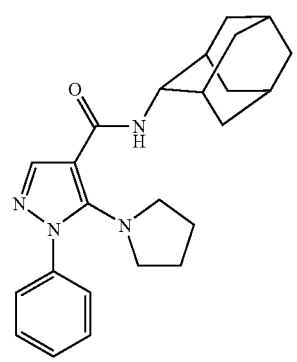

$C_{24}H_{30}N_4O$
390.53

Phenyl-5-pyrrolidin-1-yl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and pyrrolidine. Mass spectrum (ES) MH+=391.

Example 14

5-Azepan-1-yl-1-phenyl-1H-pyrazole-4-carboxylic acid adamantan-2-ylamide

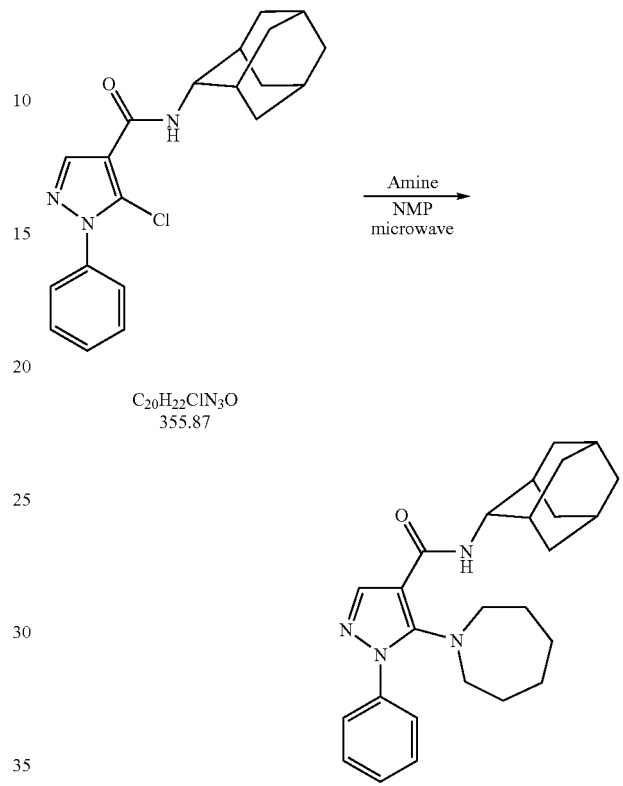

$C_{20}H_{22}ClN_3O$
355.87

$C_{26}H_{34}N_4O$
418.58

5-Azepan-1-yl-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and hexamethyleneimine. Mass spectrum (ES) MH+=419.

Example 15

5-Morpholin-4-yl-1-phenyl-1H-pyrazole-4-carboxylic acid adamantan-2-ylamide

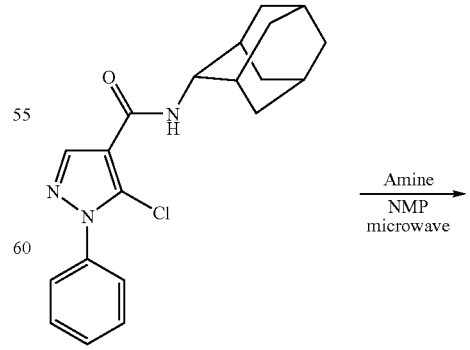

$C_{20}H_{22}ClN_3O$
355.87

-continued

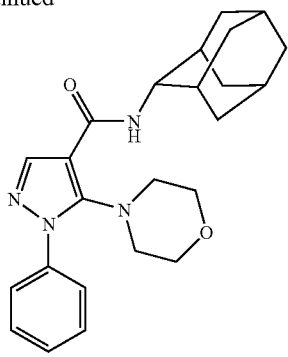

C₂₄H₃₀N₄O₂
406.53

5-Morpholin-4-yl-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and morpholine. Mass spectrum (ES) MH+=407.

Example 16

5-(3-Hydroxymethyl-piperidin-1-yl)-1-phenyl-1H-pyrazole-4-carboxylic acid adamantan-2-ylamide

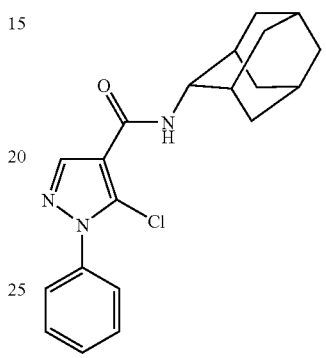

C₂₀H₂₂ClN₃O
355.87

$\xrightarrow{\text{Amine}}$ NMP microwave

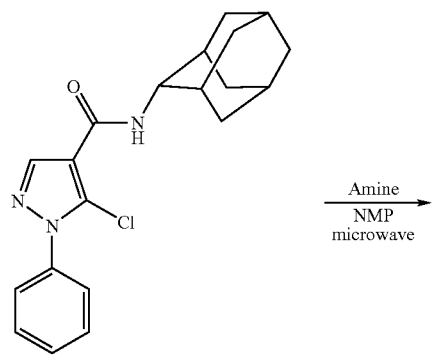

C₂₆H₃₄N₄O₂
434.58

5-(3-Hydroxymethyl-piperidin-1-yl)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and 3-piperidinemethanol. Mass spectrum (ES) MH+=435.

Example 17

5-((S)-2-Hydroxymethyl-pyrrolidin-1-yl)-1-phenyl-1H-pyrazole-4-carboxylic acid adamantan-2-ylamide

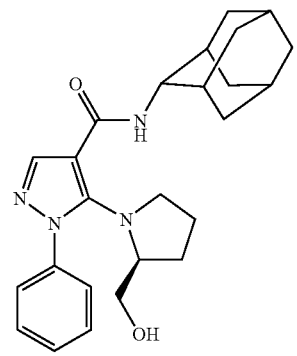

C₂₀H₂₂ClN₃O
355.87

$\xrightarrow{\text{Amine}}$ NMP microwave

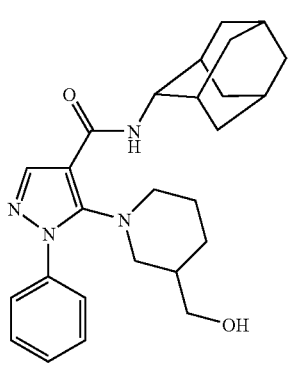

C₂₅H₃₂N₄O₂
420.55

5-((S)-2-Hydroxymethyl-pyrrolidin-1-yl)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and L-prolinol. Mass spectrum (ES) MH+=421.

Example 18

5-(4-Hydroxy-piperidin-1-yl)-1-phenyl-1H-pyrazole-4-carboxylic acid adamantan-2-ylamide

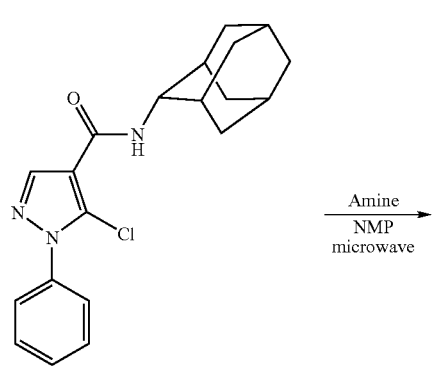

$C_{20}H_{22}ClN_3O$
355.87

→ Amine / NMP / microwave

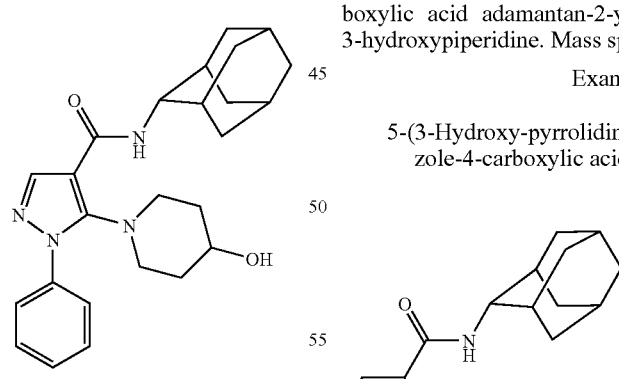

$C_{25}H_{32}N_4O_2$
420.55

5-(4-Hydroxy-piperidin-1-yl)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and 4-hydroxypiperidine. Mass spectrum (ES) MH+=421.

Example 19

5-(3-Hydroxy-piperidin-1-yl)-1-phenyl-1H-pyrazole-4-carboxylic acid adamantan-2-ylamide

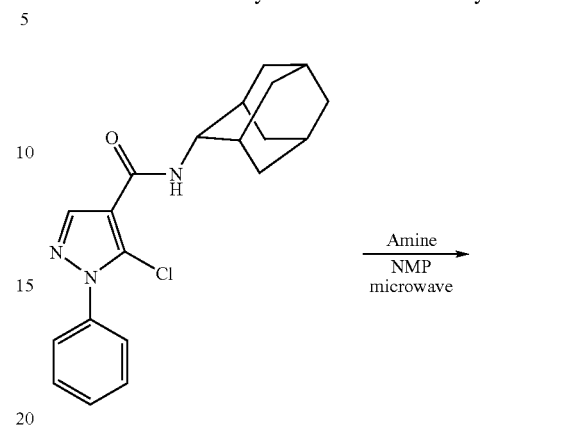

$C_{20}H_{22}ClN_3O$
355.87

→ Amine / NMP / microwave

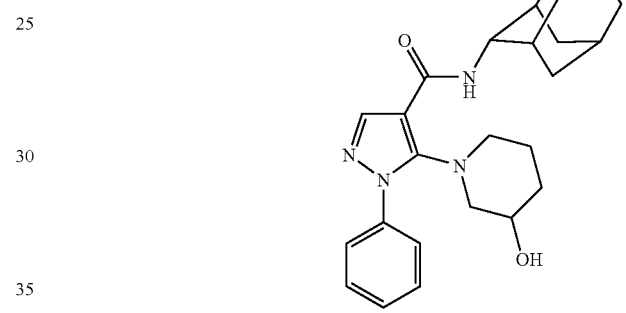

$C_{25}H_{32}N_4O_2$
420.55

5-(3-Hydroxy-piperidin-1-yl)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and 3-hydroxypiperidine. Mass spectrum (ES) MH+=421.

Example 20

5-(3-Hydroxy-pyrrolidin-1-yl)-1-phenyl-1H-pyrazole-4-carboxylic acid adamantan-2-ylamide

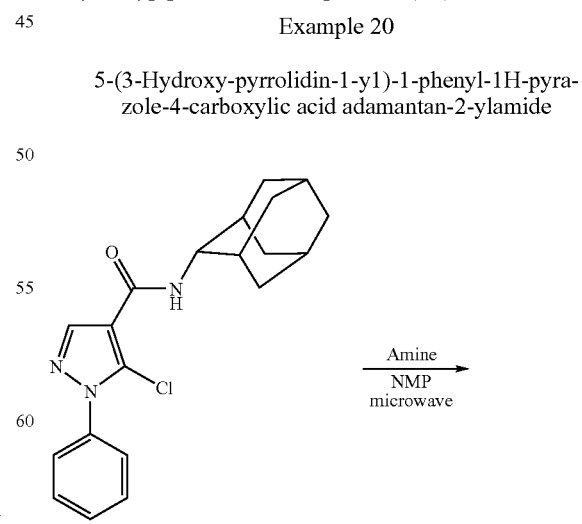

$C_{20}H_{22}ClN_3O$
355.87

→ Amine / NMP / microwave

-continued

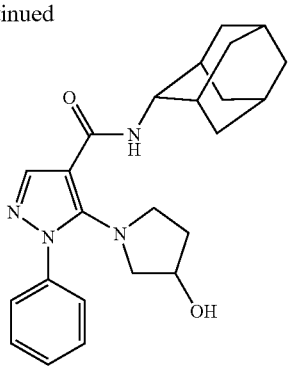

C₂₄H₃₀N₄O₂
406.53

5-(3-Hydroxy-pyrrolidin-1-yl)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and DL-3-pyrrolidinol. Mass spectrum (ES) MH+=407.

Example 21

5-(2-Hydroxy-propylamino)-1-phenyl-1H-pyrazole-4-carboxylic acid adamantan-2-ylamide

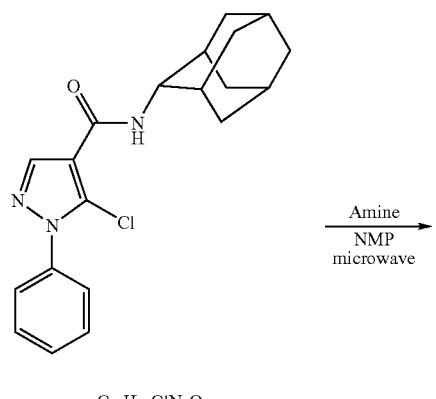

C₂₀H₂₂ClN₃O
355.87

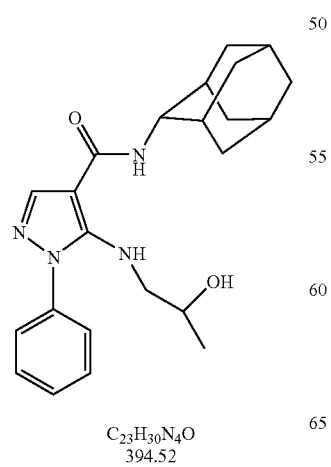

C₂₃H₃₀N₄O
394.52

5-(2-Hydroxy-propylamino)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and 1-amino-2-propanol. Mass spectrum (ES) MH+=395.

Example 22

5-(2-Hydroxy-ethylamino)-1-phenyl-1H-pyrazole-4-carboxylic acid adamantan-2-ylamide

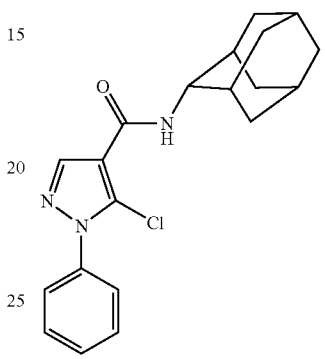

C₂₀H₂₂ClN₃O
355.87

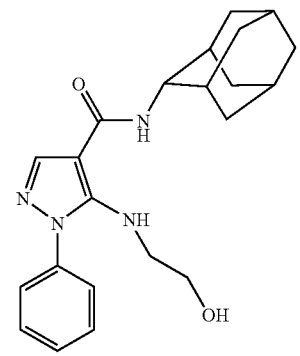

C₂₂H₂₈N₄O₂
380.49

5-(2-Hydroxy-ethylamino)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and ethanolamine. Mass spectrum (ES) MH+=381.

Example 23

5-(3-Hydroxy-propylamino)-1-phenyl-1H-pyrazole-4-carboxylic acid adamantan-2-ylamide

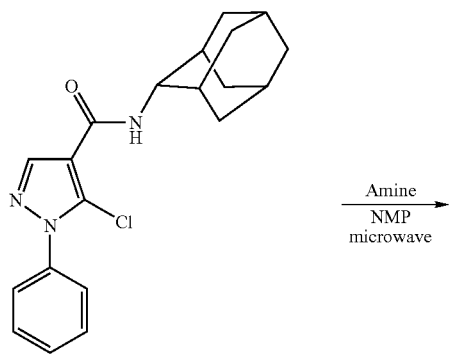

C$_{20}$H$_{22}$ClN$_3$O
355.87

Amine / NMP microwave →

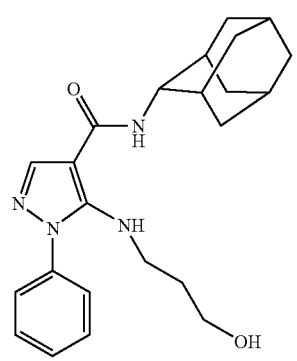

C$_{23}$H$_{30}$N$_4$O$_2$
394.52

5-(3-Hydroxy-propylamino)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and 3-amino-1-propanol. Mass spectrum (ES) MH+=395.

Example 24

5-(4-Hydroxy-butylamino)-1-phenyl-1H-pyrazole-4-carboxylic acid adamantan-2-ylamide

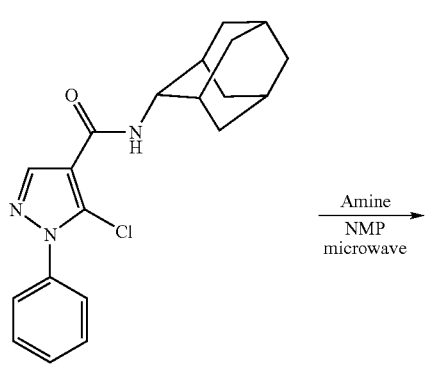

C$_{20}$H$_{22}$ClN$_3$O
355.87

Amine / NMP microwave →

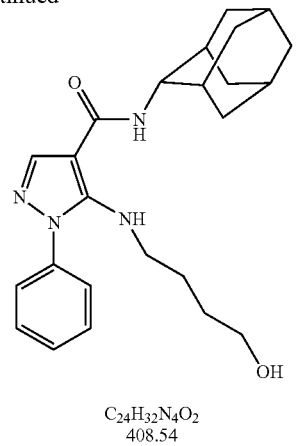

C$_{24}$H$_{32}$N$_4$O$_2$
408.54

5-(4-Hydroxy-butylamino)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and 4-amino-1-butanol. Mass spectrum (ES) MH+=409.

Example 25

1-Phenyl-5-[(tetrahydro-furan-2-ylmethyl)-amino]-1H-pyrazole-4-carboxylic acid adamantan-2-ylamide

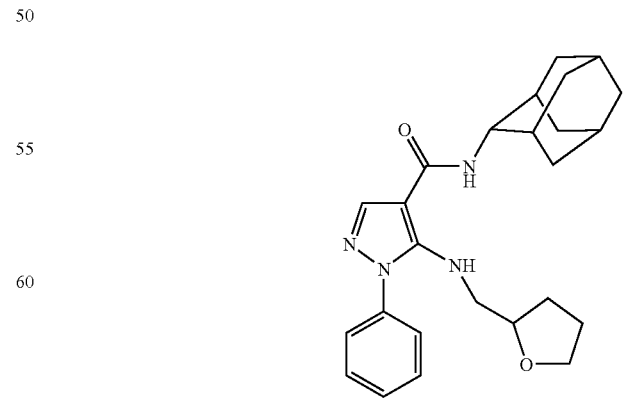

C$_{20}$H$_{22}$ClN$_3$O
355.87

Amine / NMP microwave →

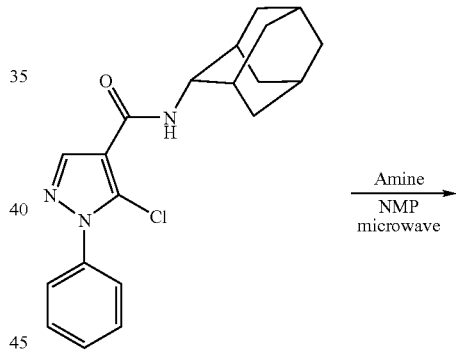

C$_{25}$H$_{32}$N$_4$O$_2$
420.55

Phenyl-5-[(tetrahydro-furan-2-ylmethyl)-amino]-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and tetrahydrofurfurylamine. Mass spectrum (ES) MH+=421.

Example 26
5-[(2-Hydroxy-ethyl)-methyl-amino]-1-phenyl-1H-pyrazole-4-carboxylic acid adamantan-2-ylamide

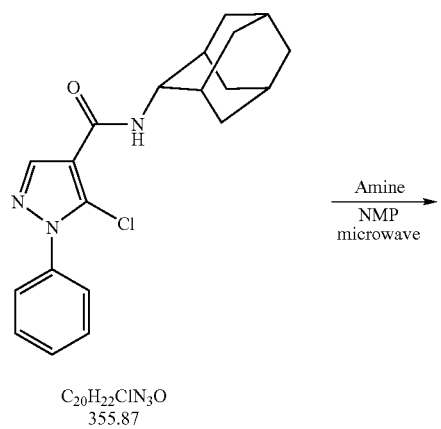

$C_{20}H_{22}ClN_3O$
355.87

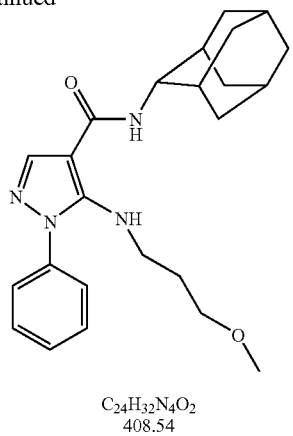

$C_{23}H_{30}N_4O_2$
394.52

5-[(2-Hydroxy-ethyl)-methyl-amino]-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and 2-(methylamino)ethanol. Mass spectrum (ES) MH+=396.

Example 27
5-(3-Methoxy-propylamino)-1-phenyl-1H-pyrazole-4-carboxylic acid adamantan-2-ylamide

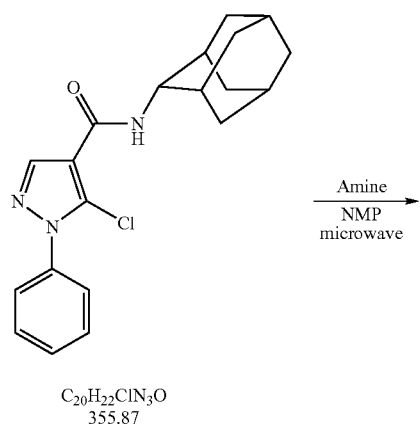

$C_{20}H_{22}ClN_3O$
355.87

$C_{24}H_{32}N_4O_2$
408.54

5-(3-Methoxy-propylamino)-1-phenyl-1H-pyrazole-4-carboxylic acid adamantan-2-ylamide was prepared using Procedure A from 5-chloro-1-phenyl-1H-pyrazole-4-carboxylic acid adamantan-2-ylamide (Intermediate 3) and 3-methoxypropylamine. Mass spectrum (ES) MH+=409.

Example 28

Testing of Compounds of the Invention in Vitro

The in vitro inhibition of 11β-HSD1 by compounds of the present invention were demonstrated by means of the following test:

H4IIE cells stably transfected with full-length human 11betaHSD1 cDNA were propagated and expanded in DMEM high glucose media (Invitrogen Cat# 11995-065), supplemented with 10% FCS (Invitrogen Cat# 10082-147), 100 units/mL and 100 μg/mL pen/strep (Invitrogen Cat#15140-122), and geneticin (800 μg/mL). One day prior to assay, cells were released from flasks using trypsin/EDTA, centrifuged, and washed with plating media (DMEM high glucose, without phenol red; Invitrogen Cat# 21063-029, supplemented with 2% charcoal stripped FCS; Gemini Cat# 100-119). From a 500,000 cells/mL suspension in plating media, 200 μL of cells were seeded into each well of a 96-well coated plate (BioCoat Cat#356461) and cultured overnight at 37° C. The following day, serially diluted 11betaHSD1 inhibitor compounds dissolved in DMSO were added to DMEM with BSA (2 mg/mL final). The final DMSO concentration was 1%. Media was aspirated from plates, and compounds in media were added to each well. The plates were incubated at 37° C. for 1 hour to allow for cellular uptake of compounds. 10 μL of substrate (cortisone) was then added to each well (200 nM final concentration) and incubated for 2 hours at 37° C. Plates were then transferred to ice and 80 μL of media transferred to a 96-well plate and stored at −30° C.

Quantitation of cortisol in cell media was performed by competitive ELISA using ELISA-Light (Tropix Cat# T10206/EL100S4), anti-cortisol EIA antibody (Assay Designs, Inc. Cat#80-1148), and cortisol-enzyme conjugate (Assay Designs, Inc. Cat# 80-1147). 384-well plates (Falcon Cat#353988) were precoated with anti-mouse IgG (Sigma Cat# M-1397) suspended in 0.9% NaCl (5 mg/mL), 50 μL per well, overnight at 4° C. Plates were washed with PBS, 0.1% Tween-20, then washed with PBS alone. Plates were blocked with Blocking Buffer (Tropix Cat# AI075) for 2 hours at room temperature. The plates were then washed as previously described. Assay samples were thawed, diluted 1:8 in DMEM, 2 mg/mL BSA, 1% DMSO, and 24 μL was transferred to wells of a pre-coated 384-well plate, as well as varying amounts of cortisol standard. To each well, 12 μL of cortisol-conjugate and 12 μL of anti-cortisol EIA antibody were added and incubated 2 hrs at room temperature on a orbital plate shaker. The wells were then emptied by inversion, then washed three times with 100 μL of PBS, 0.05% Tween-20, and then 2 times with 100 μL of Assay Buffer (Tropix). 60 μL of CDP-STAR (Tropix) was added to each well and incubated 10 minutes at room temperature. Chemiluminescence was measured using a Victor V Reader (Perkin Elmer). Cortisol in each sample was interpolated from a standard curve generated with known amounts of cortisol. $IC_{50}$ values were calculated using the curve fitting software XLFit4 (IDBS).

The results of the in vitro inhibition of 11β-HSD1 by representative compounds of the present invention are shown in the following Table

| Compound | Name | IC50 (μM) |
| --- | --- | --- |
| Example 1 | 5-Isopropylamino-1-phenyl-1H-pyrazole-4-carboxylic acid adamantan-2-ylamide | 0.0013 |
| Example 2 | 5-Benzylamino-1-phenyl-1H-pyrazole-4-carboxylic acid adamantan-2-ylamide | 0.014 |
| Example 3 | 1-Phenyl-5-[(pyridin-3-ylmethyl)-amino]-1H-pyrazole-4-carboxylic acid adamantan-2-ylamide | 0.35 |
| Example 4 | 5-(Cyclopropylmethyl-amino)-1-phenyl-1H-pyrazole-4-carboxylic acid adamantan-2-ylamide | 0.0019 |
| Example 5 | 5-Cyclohexylamino-1-phenyl-1H-pyrazole-4-carboxylic acid adamantan-2-ylamide | 0.0047 |
| Example 6 | 5-Cyclobutylamino-1-phenyl-1H-pyrazole-4-carboxylic acid adamantan-2-ylamide | 0.0076 |
| Example 7 | 5-(2,5-Dimethyl-pyrrolidin-1-yl)-1-phenyl-1H-pyrazole-4-carboxylic acid adamantan-2-ylamide | 0.004 |
| Example 8 | 5-(2-Methyl-pyrrolidin-1-yl)-1-phenyl-1H-pyrazole-4-carboxylic acid adamantan-2-ylamide | 0.0013 |
| Example 9 | 5-(3-Methyl-piperidin-1-yl)-1-phenyl-1H-pyrazole-4-carboxylic acid adamantan-2-ylamide | 0.003 |
| Example 10 | 5-(Benzyl-methyl-amino)-1-phenyl-1H-pyrazole-4-carboxylic acid adamantan-2-ylamide | 0.0091 |
| Example 11 | 5-(Methyl-phenethyl-amino)-1-phenyl-1H-pyrazole-4-carboxylic acid adamantan-2-ylamide | 0.0037 |
| Example 12 | 5-(2,6-Dimethyl-morpholin-4-yl)-1-phenyl-1H-pyrazole-4-carboxylic acid adamantan-2-ylamide | 0.0037 |
| Example 13 | 1-Phenyl-5-pyrrolidin-1-yl-1H-pyrazole-4-carboxylic acid adamantan-2-ylamide | 0.00055 |
| Example 14 | 5-Azepan-1-yl-1-phenyl-1H-pyrazole-4-carboxylic acid adamantan-2-ylamide | 0.001 |
| Example 15 | 5-Morpholin-4-yl-1-phenyl-1H-pyrazole-4-carboxylic acid adamantan-2-ylamide | 0.003 |
| Example 16 | 5-(3-Hydroxymethyl-piperidin-1-yl)-1-phenyl-1H-pyrazole-4-carboxylic acid adamantan-2-ylamide | 0.0064 |
| Example 17 | 5-((S)-2-Hydroxymethyl-pyrrolidin-1-yl)-1-phenyl-1H-pyrazole-4-carboxylic acid adamantan-2-ylamide | 0.042 |
| Example 18 | 5-(4-Hydroxy-piperidin-1-yl)-1-phenyl-1H-pyrazole-4-carboxylic acid adamantan-2-ylamide | 0.003 |
| Example 19 | 5-(3-Hydroxy-piperidin-1-yl)-1-phenyl-1H-pyrazole-4-carboxylic acid adamantan-2-ylamide | 0.0092 |
| Example 20 | 5-(3-Hydroxy-pyrrolidin-1-yl)-1-phenyl-1H-pyrazole-4-carboxylic acid adamantan-2-ylamide | 0.013 |
| Example 21 | 5-(2-Hydroxy-propylamino)-1-phenyl-1H-pyrazole-4-carboxylic acid adamantan-2-ylamide | 0.041 |
| Example 22 | 5-(2-Hydroxy-ethylamino)-1-phenyl-1H-pyrazole-4-carboxylic acid adamantan-2-ylamide | 0.021 |
| Example 23 | 5-(3-Hydroxy-propylamino)-1-phenyl-1H-pyrazole-4-carboxylic acid adamantan-2-ylamide | 0.055 |
| Example 24 | 5-(4-Hydroxy-butylamino)-1-phenyl-1H-pyrazole-4-carboxylic acid adamantan-2-ylamide | 0.0075 |
| Example 25 | 1-Phenyl-5-[(tetrahydro-furan-2-ylmethyl)-amino]-1H-pyrazole-4-carboxylic acid adamantan-2-ylamide | 0.002 |
| Example 26 | 5-[(2-Hydroxy-ethyl)-methyl-amino]-1-phenyl-1H-pyrazole-4-carboxylic acid adamantan-2-ylamide | 0.014 |
| Example 27 | 5-(3-Methoxy-propylamino)-1-phenyl-1H-pyrazole-4-carboxylic acid adamantan-2-ylamide | 0.0014 |

What is claimed is:

1. A compound of formula (I):

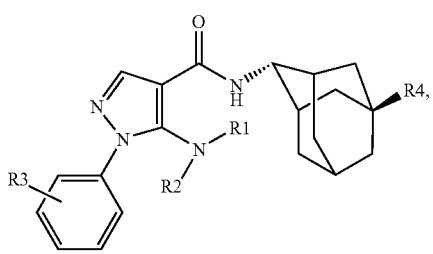

wherein:
- $R_1$ is H or lower alkyl;
- $R_2$ is lower alkyl, —$(CH_2)_n$-cycloalkyl, —$(CH_2)_n$-heterocycloalkyl, —$(CH_2)_n$-aryl, —$(CH_2)_n$-heteroaryl, —$(CH_2)_n$OH, —$(CH_2)_n$CH($CH_3$)OH or —$(CH_2)_n$OCH$_3$;

or

- $R_1$ and $R_2$, together with the N atom to which they are attached, form a 5- to 7-membered monocyclic ring, which contains the N atom to which $R_1$ and $R_2$ are attached, and optionally another hetero atom which is selected from O and S, unsubstituted or mono- or bi- substituted with hydroxy, lower alkyl or —$(CH_2)_n$OH;
- $R_3$ is one or more substituents selected from H, halogen, lower alkyl and lower alkoxy;
- $R_4$ is H, OH, NHC(=O)CH$_3$ or NHS(=O)(=O)CH$_3$;
- n is 1, 2, 3 or 4;

and pharmaceutically acceptable salt thereof.

2. The compound according to claim 1, wherein $R_1$ is H and $R_2$ is lower alkyl, —$(CH_2)_n$-cycloalkyl, —$(CH_2)_n$-heterocycloalkyl, —$(CH_2)_n$-aryl, —$(CH_2)_n$-heteroaryl, —$(CH_2)_n$OH, —$(CH_2)_n$CH($CH_3$)OH or —$(CH_2)_n$OCH$_3$.

3. The compound according to claim 1, wherein $R_1$ is lower alkyl and $R_2$ is lower alkyl, —$(CH_2)_n$-cycloalkyl, —$(CH_2)_n$-heterocycloalkyl, —$(CH_2)_n$-aryl, —$(CH_2)_n$-heteroaryl, —$(CH_2)_n$OH, —$(CH_2)_n$CH($CH_3$)OH or —$(CH_2)_n$OCH$_3$.

4. The compound according to claim 1, wherein $R_1$ is methyl.

5. The compound according to claim 1, wherein $R_1$ and $R_2$, together with the N atom to which they are attached, form an unsubstituted 5- to 7-membered monocyclic ring, which contains the N atom to which $R_1$ and $R_2$ are attached.

6. The compound according to claim 1, wherein $R_1$ and $R_2$, together with the N atom to which they are attached, form an unsubstituted 5- to 7-membered monocyclic ring, which contains the N atom to which $R_1$ and $R_2$ are attached and another hetero atom which is selected from O and S.

7. The compound according to claim 1, wherein $R_1$ and $R_2$, together with the N atom to which they are attached, form a 5- to 7-membered monocyclic ring, which contains the N atom to which $R_1$ and $R_2$ are attached, mono- or bi- substituted with hydroxy, lower alkyl or —$(CH_2)_n$OH.

8. The compound according to claim 1, wherein $R_1$ and $R_2$, together with the N atom to which they are attached, form a 5- to 7-membered monocyclic ring, which contains the N atom to which $R_1$ and $R_2$ are attached, and another hetero atom which is selected from O and S, mono- or bi- substituted with hydroxy, lower alkyl or —$(CH_2)_n$OH.

9. The compound according to claim 1, wherein $R_2$ is isopropyl, —$CH_2$-phenyl, —$CH_2$-pyridinyl, —$CH_2$-cyclopropyl, cyclohexyl, cyclobutyl, —$CH_2CH_2$-phenyl, hydroxypropyl, hydroxyethyl, hydroxybutyl, —$CH_2$-tetrahydrofuran or methoxypropyl.

10. The compound according to claim 1, wherein —$NR_1R_2$ is pyrrolidinyl, dimethylpyrrolidinyl, methylpyrrolidinyl, methylpiperidinyl, morpholinyl, dimethylmorpholinyl, azepanyl, hydroxymethylpiperidinyl, hydroxymethylpyrrolidinyl, hydroxypiperidinyl or hydroxypyrrolidinyl.

11. The compound according to claim 1, wherein $R_3$ is hydrogen or halogen.

12. The compound according to claim 1, wherein $R_4$ is H, OH, or NHC(=O)CH$_3$.

13. The compound according to claim 1, wherein said compound is:
- 5-Isopropylamino-1-phenyl-1H-pyrazole-4-carboxylic acid adamantan-2-ylamide;
- 5-(Cyclopropylmethyl-amino)-1-phenyl-1H-pyrazole-4-carboxylic acid adamantan-2-ylamide;
- 5-(2-Methyl-pyrrolidin-1-yl)-1-phenyl-1H-pyrazole-4-carboxylic acid adamantan-2-ylamide;
- 5-(3-Methyl-piperidin-1-yl)-1-phenyl-1H-pyrazole-4-carboxylic acid adamantan-2-ylamide;
- 1-Phenyl-5-pyrrolidin-1-yl-1H-pyrazole-4-carboxylic acid adamantan-2-ylamide;
- 5-Azepan-1-yl-1-phenyl-1H-pyrazole-4-carboxylic acid adamantan-2-ylamide;
- 5-Morpholin-4-yl-1-phenyl-1H-pyrazole-4-carboxylic acid adamantan-2-ylamide;
- 5-(4-Hydroxy-piperidin-1-yl)-1-phenyl-1H-pyrazole-4-carboxylic acid adamantan-2-ylamide;
- 1-Phenyl-5-[(tetrahydro-furan-2-ylmethyl)-amino]-1H-pyrazole-4-carboxylic acid adamantan-2-ylamide; or
- 5-(3-Methoxy-propylamino)-1-phenyl-1H-pyrazole-4-carboxylic acid adamantan-2-ylamide.

14. A pharmaceutical composition, comprising a therapeutically effective amount of a compound according to claim 1, or a pharmaceutically acceptable salt thereof, and a pharmaceutically acceptable carrier.

15. A method for treating diabetes, comprising the step of administering a therapeutically effective amount of a compound according to claim 1, or a pharmaceutically acceptable salt thereof, to a patient in need thereof.

* * * * *